(12) United States Patent
Curtis et al.

(10) Patent No.: US 11,211,149 B2
(45) Date of Patent: Dec. 28, 2021

(54) FILTERING GENETIC NETWORKS TO DISCOVER POPULATIONS OF INTEREST

(71) Applicant: ANCESTRY.COM DNA, LLC, Lehi, UT (US)

(72) Inventors: Ross E. Curtis, Cedar Hills, UT (US); Ahna R. Girshick, Berkeley, CA (US); Ariel Hippen Anderson, Provo, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 17/252,652

(22) PCT Filed: Jun. 14, 2019

(86) PCT No.: PCT/IB2019/054975
§ 371 (c)(1),
(2) Date: Dec. 15, 2020

(87) PCT Pub. No.: WO2019/243969
PCT Pub. Date: Dec. 26, 2019

(65) Prior Publication Data
US 2021/0257060 A1    Aug. 19, 2021

Related U.S. Application Data

(60) Provisional application No. 62/687,177, filed on Jun. 19, 2018.

(51) Int. Cl.
*G16B 45/00*      (2019.01)
*G16B 40/00*      (2019.01)
*G16B 10/00*      (2019.01)
*G16B 20/40*      (2019.01)

(52) U.S. Cl.
CPC ............ *G16B 45/00* (2019.02); *G16B 10/00* (2019.02); *G16B 20/40* (2019.02); *G16B 40/00* (2019.02)

(58) Field of Classification Search
CPC ........ G16B 45/00; G16B 10/00; G16B 40/00; G16B 20/40
USPC ........................................................ 702/19
See application file for complete search history.

(56) References Cited

U.S. PATENT DOCUMENTS

| 6,570,567 | B1 | 5/2003 | Eaton |
| 7,062,752 | B2 | 6/2006 | Simpson et al. |
| 7,249,129 | B2 | 7/2007 | Cookson et al. |
| 7,818,281 | B2 | 10/2010 | Kennedy et al. |
| 8,510,057 | B1 | 8/2013 | Avey et al. |
| 8,769,438 | B2 | 7/2014 | Mangum |
| 9,116,882 | B1 | 8/2015 | Macpherson et al. |
| 9,213,947 | B1 | 12/2015 | Do et al. |
| 9,336,177 | B2 | 5/2016 | Hawthorne et al. |
| 9,367,800 | B1 | 6/2016 | Do et al. |
| 9,836,576 | B1 | 12/2017 | Do et al. |
| 9,864,835 | B2 | 1/2018 | Avey et al. |
| 10,025,877 | B2 | 7/2018 | Macpherson |
| 2002/0019746 | A1 | 2/2002 | Rienhoff et al. |
| 2002/0143578 | A1 | 10/2002 | Cole et al. |
| 2003/0101000 | A1 | 5/2003 | Bader et al. |
| 2003/0113727 | A1 | 6/2003 | Girn et al. |
| 2003/0172065 | A1 | 9/2003 | Sorenson et al. |
| 2004/0083226 | A1 | 4/2004 | Eaton |
| 2004/0093334 | A1 | 5/2004 | Scherer |
| 2004/0126840 | A1 | 7/2004 | Cheng et al. |
| 2005/0089852 | A1 | 4/2005 | Lee et al. |
| 2005/0147947 | A1 | 7/2005 | Cookson et al. |
| 2005/0164704 | A1 | 7/2005 | Winsor |
| 2005/0164705 | A1 | 7/2005 | Rajkotia et al. |
| 2005/0192008 | A1 | 9/2005 | Desai et al. |
| 2007/0050354 | A1 | 3/2007 | Rosenberg |
| 2007/0260599 | A1 | 11/2007 | McGuire et al. |
| 2008/0040046 | A1 | 2/2008 | Chakraborty et al. |
| 2008/0081331 | A1 | 4/2008 | Myres et al. |
| 2008/0082955 | A1 | 4/2008 | Andreessen et al. |
| 2008/0113727 | A1 | 5/2008 | Vallejo et al. |
| 2008/0154566 | A1 | 6/2008 | Myres et al. |
| 2008/0162510 | A1 | 7/2008 | Baio et al. |

(Continued)

FOREIGN PATENT DOCUMENTS

WO    WO 02/17190 A1    2/2002
WO    WO 2014-145280 A1    9/2014

OTHER PUBLICATIONS

Alexander, D.H. et al., "Enhancements to the ADMIXTURE Algorithm for Individual Ancestry Estimation," BMC Bioinformatics 12(1), 246, Jun. 18, 2011, pp. 1-6.

Alexander, D.H., et al., "Fast model-based estimation of ancestry in unrelated individuals," Genome research, Sep. 2009, vol. 19, No. 9, pp. 1655-1664.

Atzmon, G. et al., "Abraham's Children in the Genome Era: Major Jewish Diaspora Populations Comprise Distinct Genetic Clusters with Shared Middle Eastern Ancestry," American Journal of Human Genetics 86(6), Jun. 11, 2010, pp. 850-859.

(Continued)

*Primary Examiner* — Jerry Lin
(74) *Attorney, Agent, or Firm* — Fenwick & West LLP

(57) ABSTRACT

A computing server generates a graph such as an identity-by-descent (IBD) network. The graph includes a plurality of nodes. Each node represents one of the individuals. Two or more nodes are connected through edges. Each edge connecting two nodes and associated with a weight that is derived from affinity between the genetic data of the two individuals represented by the two nodes. The computing system filters the graph based on features that are associated with the edges or the nodes. The filtered graph includes a subset of nodes. The computing system divides the filtered graph into a plurality of clusters to identify genetic communities that may not be discoverable without filtering. The computing server may also perform a multi-path hierarchical community detection process to assign an individual represented by a node to more than one communities.

20 Claims, 13 Drawing Sheets

(56) References Cited

U.S. PATENT DOCUMENTS

| | | |
|---|---|---|
| 2008/0255768 A1 | 10/2008 | Martin et al. |
| 2009/0030985 A1 | 1/2009 | Yuan |
| 2012/0054190 A1 | 3/2012 | Peters |
| 2012/0191903 A1 | 7/2012 | Araki et al. |
| 2013/0085728 A1 | 4/2013 | Tang et al. |
| 2013/0149707 A1 | 6/2013 | Sorenson et al. |
| 2014/0082568 A1 | 3/2014 | Hulet et al. |
| 2014/0108527 A1 | 4/2014 | Aravanis et al. |
| 2014/0278138 A1 | 9/2014 | Barber et al. |
| 2016/0350479 A1 | 12/2016 | Han et al. |
| 2018/0011970 A1 | 1/2018 | Dowds et al. |

OTHER PUBLICATIONS

Belkin, M. et al., "Laplacian Eigenmaps for Dimensionality Reduction and Data Representation," Neural Computation Jun. 15, 2003, pp. 1373-1396.

Bengio, Y. et al., "Out-of-Sample Extensions for LLE, Isomap, MOS, Eigenmaps and Spectral Clustering," NIPS'03: Proceedings of the 16th International Conference on Neural Information Processing Systems, Dec. 2003, pp. 177-184.

Blondel, V.D. et al., "Fast Unfolding of Community Hierarchies in Large Networks," Journal of Statistical Mechanics: Theory and Experiment, Oct. 9, 2008, p. 1-12.

Browning, B.L et al., "Efficient Multilocus Association Testing for Whole Genome Association Studies Using Localized Haplotype Clustering," Genetic Epidemiology, vol. 31, Feb. 26, 2007, pp. 365-375.

Browning, S.R. et al., "High-resolution detection of Identity by Descent in unrelated individuals," The American Journal of Human Genetics, vol. 86, Apr. 9, 2010, pp. 526-539.

Browning, S.R. et al., "Rapid and Accurate Haplotype Phasing and Missing-Data Inference for Whole-Genome Association Studies by Use of Localized Haplotype Clustering," American Journal of Human Genetics, vol. 81, Nov. 2007, pp. 1084-1097.

Browning, S.R., "Multilocus Association Mapping Using Variable-Length Markov Chains," The American Journal of Human Genetics, Jun. 2006, vol. 78, pp. 903-913.

Cann, H.M. et al., "A human genome diversity cell line panel," Science, Apr. 2002, vol. 296, No. 5566, pp. 261-262.

Carmi, S. et al., "Sequencing an Ashkenazi Reference Panel Supports Population-Targeted Personal Genomics and Illuminates Jewish and European Origins," Nature Communications 5:4835, Sep. 9, 2014, pp. 1-9.

Carmi, S. et al., "The Variance of Identity-by-Descent Sharing in the Wright-Fsher Model," Genetics 193(3), Mar. 2013, pp. 911-928.

Cavalli-Sforza, L.L. "The human genome diversity project: past, present and future," Nature Reviews Genetics, Apr. 2005, vol. 6, No. 4. pp. 333-340.

Coifman, R.R. et al., "Diffusion Maps," Applied and Computational Harmonic Analysis, vol. 21, Jun. 19, 2006, pp. 5-30.

Dudoit, et al., "A score test for the linkage analysis of qualitative and quantitative traits based on identity by descent data from sib-pairs," Biostatistics, vol. 1, Iss. 1, Mar. 2000, pp. 1-26.

Durand, E.Y. et al., "Reducing Pervasive False-Positive Identical-by-Descent Segments Detected by Large-Scale Pedigree Analysis," Molecular Biology and Evolution 31(8), Apr. 30, 2014, pp. 2212-2222.

Falush, D. et al., "Inference of Population Structure Using Multilocus Genotype Data: Linked Loci and Correlated Allele Frequencies," Genetics, vol. 164, Aug. 2003, pp. 1567-1587.

Fortunato, S. et al., "Resolution Limit in Community Detection," Proceedings of the National Academy of Sciences 104(1), Jan. 2, 2007, pp. 36-41.

Fortunato, S., "Community Detection in Graphs," Physics Reports 486, Dec. 4, 2009, pp. 75-174.

Francioli, L. et al., Whole-Genome Sequence Variation, Population Structure and Demographic History of the Dutch Population, Nature Genetics 46(8), Aug. 2014, pp. 818-825.

Gauvin, H. et al., "Genome-Wide Patterns of Identity-by-Descent Sharing in the French Canadian Founder Population," European Journal of Human Genetics 22, Oct. 16, 2013, pp. 814-821.

Girvan, M. et al., "Community Structure in Social and Biological Networks," PNAS 99(12), Jun. 11, 2002, pp. 7821-7826.

Good, B.H. et al., "Performance of Modularity Maximization in Practical Contexts," Physical Review E 81(4), Apr. 15, 2010, pp. 1-19.

Gusev, A. et al., "Whole Population, Genome-Wide Mapping of Hidden Relatedness," Genome Research 19(2), Feb. 2009, pp. 318-326.

Han, L. et al., "Identity by descent estimation with dense genome-wide genotype data," Genet Epidemiol., vol. 35, No. 6, Sep. 2011, pp. 557-567.

Hao, W. et al., "Probabilistic Models of Genetic Variation in Structured Populations Applied to Global Human Studies," arXiv:1312.2041, Dec. 7, 2013, pp. 1-35.

International HapMap Consortium, "A haplotype map of the human genome," Nature, Oct. 2005, vol. 437, No. 27, pp. 1299-1320.

International HapMap Consortium, "A second generation human haplotype map of over 3.1 million SNPs," Nature, Oct. 2007, vol. 449, No. 7164, pp. 1-30.

Jarvis, J.P. et al., "Patterns of Ancestry of Natural Selection and Genetic Association with Stature in Western African Pygmies," PLoS Genetics, vol. 8, Iss. 4, Apr. 26, 2012, pp. 1-15.

Lee, A.B. et al., "A Spectral Graph Approach to Discovering Genetic Ancestry," Annals of Applied Statistics 4(1), Mar. 2010, pp. 179-202.

Lee, A.B. et al., "Discovering Genetic Ancestry Using Spectral Graph Theory," Genetic Epidemiology 34, May 19, 2009, pp. 51-59.

Mcgraw, P.N. et al., "Laplacian Spectra as a Diagnostic Tool for Network Structure and Dynamics," Physical Review E 77(3), Mar. 4, 2008, pp. 1-14.

Mcvean, G., "A Genealogical Interpretation of Principal Components Analysis," PLoS Genetics 5(10), Oct. 16, 2009, pp. 1-10.

Meirmans, P.G., "The Trouble with Isolation by Distance," Molecular Ecology 21(12), May 11, 2012, pp. 2839-2846.

Morrison, A.C. et al., "Prediction of Coronary Heart Disease Risk using a Genetic Risk Score: The Atherosclerosis Risk in Communities Study," American Journal of Epidemiology, vol. 166, No. 1, Apr. 18, 2007, pp. 28-35.

Newman, M.E.J., "Communities, Modules and Large-Scale Structure in Networks," Nature Physics 8(1), Jan. 2012, pp. 25-31.

Novembre, J. et al., "Genes Mirror Geography within Europe," Nature 456(7218), Nov. 2008, pp. 98-101.

Palamara, P.F. et al., "Inference of Historical Migration Rates Via Haplotype Sharing," Bioinformatics 29(13), Jul. 2013, pp. 180-188.

Palamara, P.F. et al., "Length Distributions of Identity by Descent Reveal Fine-Scale Demographic History," American Journal of Human Genetics 91(5), Nov. 2, 2012, pp. 809-822.

Palin, K. et al., "Identity-by-Descent-Based Phasing and Imputation in Founder Populations Using Graphical Models," Genetic Epidemiology, vol. 35, Oct. 17, 2011, pp. 853-860.

Patterson, N. et al., "Population structure and eigenanalysis," PLoS genetics, Dec. 2006, vol. 2, No. 12, pp. 2074-2093.

PCT International Search Report and Written Opinion, PCT Application No. PCT/IB2016/053166, dated Sep. 6, 2016, 13 pages.

Platt, J.C., "Probabilistic Outputs for Support Vector Machines and Comparisons to Regularized Likelihood Methods," Mar. 26, 1999, pp. 1-11.

Price, A.L. et al., "Sensitive Detection of Chromosomal Segments of Distinct Ancestry in Admixed Populations," PLoS Genetics, vol. 5, Iss. 6, Jun. 2009, pp. 1-18.

Pritchard, J.K. et al., "Inference of population structure using multilocus genotype data," Genetics Society of America, Jun. 2000, vol. 155, No. 2, pp. 945-959.

Purcell, S. et al., "PLINK: A tool set for whole-genome association and population-based linkage analyses," The American Journal of Human Genetics, vol. 81, Sep. 2007, pp. 559-575.

Purcell, S., "PLINK (1.07) Documentation," May 10, 2010, 293 pages, http://pnga.mgh.harvard.edu/purcell/plink/.

(56) References Cited

OTHER PUBLICATIONS

Qian, Y. et al., "Efficient clustering of identity-by-descent between multiple individuals," Bioinformatics, vol. 30, No. 7, Dec. 19, 2013, pp. 915-922.
Rabiner, L.R., "A Tutorial on Hidden Markov Models and Selected Applications in Speech Recognition," Proceedings of the IEEE, vol. 77, No. 2, Feb. 1989, pp. 257-286.
Raj, A. et al., "FastSTRUCTURE: Variational Inference of Population Structure in Large SNP Data Sets," Genetics 197(2), Jun. 2014, pp. 573-589.
Ron, D. et al., "On the Learnability and Usage of Acyclic Probabilistic Finite Automata," Journal of Computer and System Sciences, vol. 56, 1998, pp. 133-152.
Scheet, P. et al., "A Fast and Flexible Statistical Model for Large-Scale Population Genotype Data: Applications to Inferring Missing Genotypes and Haplotypic Phase," The American Journal of Human Genetics, vol. 78, Feb. 17, 2006, pp. 629-644.
Seligsohn, U. et al., "Genetic Susceptibility to Venous Thrombosis," The New England Journal of Medicine, vol. 344, No. 16, Apr. 19, 2001, pp. 1222-1231.
Staples, J. et al., "PRIMUS: Rapid Reconstruction of Pedigrees from Genome-wide Estimates of Identity by Descent," The American Journal of Human Genetics, vol. 95, Nov. 6, 2014, pp. 553-564.
Sundquist, A. et al., "Effect of Genetic Divergence in Identifying Ancestral Origin using HAPAA," Genome Res., vol. 18, Mar. 18, 2008, pp. 676-682.
The 1000 Genomes Project Consortium, "An Integrated Map of Genetic Variation from 1,092 Human Genomes," Nature 491, Nov. 2012, pp. 56-65.
The International Hapmap 3 Consortium, "Integrating common and rare genetic variation in diverse human populations," Nature, vol. 467, Sep. 2, 2010, pp. 52-58.
Tipping, M.E., "Sparse Bayesian Learning and the Relevance Vector Machine," Journal of Machine Learning Research, Jun. 2001, pp. 211-244.
U.S. Appl. No. 61/724,228, filed Nov. 8, 2012, Inventor Chuong Do.
U.S. Appl. No. 61/724,236, filed Nov. 8, 2012, Inventor Chuong Do.
Visscher, P.M et al., "Heritability in the genomics era-concepts and misconceptions," Nature Reviews Genetics, Mar. 4, 2008, pp. 255-266.
Von Luxburg, U., "A Tutorial on Spectral Clustering," Statistics and Computing 17(4), Aug. 22, 2007, pp. 395-416.
Weedon, M.N. et al., "Combining Information from Common Type 2 Diabetes Risk Polymorphisms Improves Disease Prediction," PLoS Med., vol. 3, Iss. 10, Oct. 2006, pp. 1877-1882.
Welch, B.L., "The Generalization of "Student's" Problem when Several Different Population Variances are Involved," Biometrika 34(1-2), 1947, pp. 28-35.
Williams, A.L. et al., "Phasing of Many Thousands of Genotyped Samples," The American Journal of Human Genetics, Aug. 10, 2012, vol. 91, pp. 238-251.
Yang, Q. et al., "Improving the Prediction of Complex Diseases by Testing for Multiple Disease-Susceptibility Genes," American Journal of Human Genetics, vol. 72, Feb. 14, 2003, pp. 636-649.
Yoon, B.-J., "Hidden Markov Models and their Applications in Biological Sequence Analysis," Current Genomics, vol. 10, Sep. 2009, pp. 402-415.
Zelnik-Manor, L. et al., "Self-Tuning Spectral Clustering," In Advances in Neural Information Processing Systems, Jan. 17, 2004, pp. 1601-1608.
Zhang, J., "Ancestral Informative Marker Selection and Population Structure Visualization Using Sparse Laplacian Eigenfunctions," PLoS One 5(11), Nov. 4, 2010, pp. 1-12.
Zhao, F. et al., "Spectral Clustering with Eigenvector Selection Based on Entropy Ranking," Neurocomputing 73(10-12), Mar. 12, 2010, pp. 1704-1717.
PCT International Search Report and Written Opinion, International Application No. PCT/IB2019/054975, dated Oct. 29, 2019, 10 Pages.
Browning, B.L., et al., "A Fast, Powerful Method for Detecting Identity by Descent," The American Journal of Human Genetics, Feb. 11, 2011, vol. 88, pp. 173-182.

FILTERING GENETIC NETWORKS TO DISCOVER POPULATIONS OF INTEREST

CROSS-REFERENCE TO RELATED APPLICATION

The present application claims the benefit of U.S. Provisional Patent Application 62/687,177 filed on Jun. 19, 2018, which is hereby incorporated by reference in its entirety.

BACKGROUND

The disclosed embodiments relate to assessing populations in which variants of interest may have arisen and propagated and discovering historical populations from the pattern of genetic relationships between people.

Although humans are, genetically speaking, almost entirely identical, small differences in human DNA are responsible for some observed variations between individuals. The human genome mutation rate is estimated to be $1.1*10^{-8}$ per site per generation. This leads to a variant approximately every 300 base pairs. Most of the mutations that are passed down to descendants are related to single-nucleotide polymorphism (SNP). SNP is a substitution of a single nucleotide that occurs at a specific position in the genome. Learning about population structure from genetic polymorphism data is an important topic in genetics.

SUMMARY

Disclosed herein relates to generating a graph that represents individuals and genetic relationships among the individuals to discover new genetic communities among different populations and to assign admixed individuals to more than one genetic community. In one embodiment, a computing server performs a method that includes retrieving a plurality of genetic datasets corresponding to a plurality of individuals. The computing server generates data representing a full graph. The full graph includes a plurality of nodes. Each node represents one of the individuals and the corresponding genetic dataset. Two or more nodes are connected through edges. An edge connects two nodes and is associated with a weight that is derived from affinity between the genetic datasets of the two individuals represented by the two nodes. The computing server filters the data representing the full graph based on one or more features associated with the edges or with the nodes. The filtered data represents a filtered graph comprising a subset of nodes. The computing server divides the subset of nodes in the filtered graph into a plurality of clusters based on the weights of the edges connecting the nodes in the subset. Each cluster represents a genetic community.

In another embodiment, a computing server retrieves a plurality of genetic datasets corresponding to a plurality of individuals. One of the individuals is an admixed individual. The computing server generates data representing a graph. The graph likewise includes a plurality of nodes that represent the individuals. Two or more nodes are connected through edges that are associated with weights derived from affinity between the genetic datasets of the two individuals represented by the two nodes. The plurality of nodes includes a target node that represents the admixed individual and other target nodes that represent other individuals. The computing server divides the nodes in the graph into a plurality of clusters based on the weights of the edges connecting the nodes. The plurality of clusters represents a plurality of genetic communities. The computing server includes the target node in one or more clusters representing one or more genetic communities. For at least one of the clusters in which the target node is included, the computing server divides the cluster into a plurality of sub-clusters. The target node may be classified into one or more sub-clusters in each of the one or more clusters. This represents that the admixed individual being classified into one or more different genetic sub-communities of one or more ethnic origins.

In yet another embodiment, a computing server retrieves a genetic dataset of a target individual. The computing server retrieves a plurality of reference panel samples. Each reference panel sample represents a reference panel individual. At least some of the reference panel individuals are generated from a filtered IBD network that is filtered from a full IBD network. The filtered IBD network includes a subset of nodes filtered based on one or more features of the edges or the nodes. The computing server generates a plurality of IBD affinities associated with the target individual. Each IBD affinity is determined by comparing the genetic dataset of the target individual to one of the reference panel samples. The computing server retrieves one or more community classifiers. Each community classifier is a model that is configured to determine whether an individual belongs to a genetic community. The computing server generates a set of features for each community classifier. The set of features may be generated based on the plurality of IBD affinities. The computing server inputs, for each community classifier, the set of features into the community classifier to determine whether the target individual belongs to the genetic community. The computing server generates a report summarizing one or more genetic communities to which the target individual belongs.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Example System Environment

Figure 1:
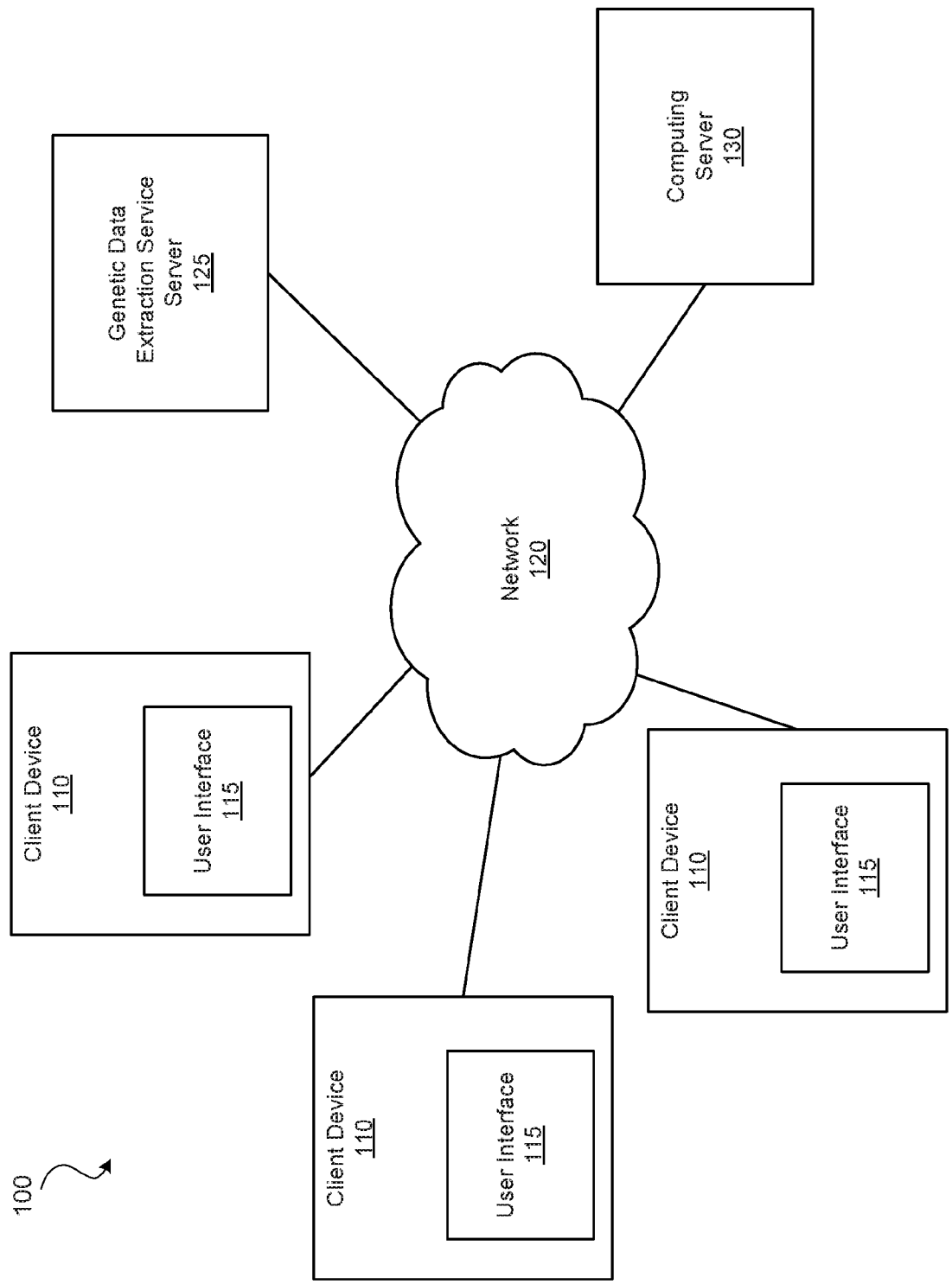
FIG. 1 illustrates a diagram of a system environment of an example computing system, in accordance with an embodiment.

FIG. 1 illustrates a diagram of a system environment 100 of an example computing server 130, in accordance with an embodiment. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliance (e.g., smart televisions, smart speakers, smart home hubs), Internet of Things (IoT) devices or other suitable electronic devices. A client device 110 communicates to other components via the network 120. In one embodiment, a client device 110 executes an application that launches a graphical user interface (GUI) for a user of the client device 110 to interact with the computing server 130 via a user interface 115 of the client device. For example, a client device 110 may execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In one embodiment, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 130 also includes links and packet switching networks such as the Internet.

Individuals who may be customers of a company operating the computing server 130 provide biological samples for analysis of their genetic data. In one embodiment, an individual uses a sample collection kit to provide a biological sample (e.g., saliva, blood, hair, tissue) from which genetic data is extracted according to nucleotide processing techniques such as amplification and sequencing. Amplification may include using polymerase chain reaction (PCR) to may amplify segments of nucleotide samples. Sequencing may include sequencing of deoxyribonucleic acid (DNA) sequencing, ribonucleic acid (RNA) sequencing, etc. Sequencing of nucleotide samples may include Sanger sequencing and massively parallel sequencing such as various next-generation sequencing (NGS) techniques including whole genome sequencing, pyrosequencing, sequencing by synthesis, sequencing by ligation, and ion semiconductor sequencing. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from expression and/or non-expression regions of DNA.

The genetic data may take different forms. For example, in one embodiment, the genetic data may be the base pair sequence of an individual. The base pair sequence may include the whole genome or a part of the genome such as genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. In one embodiment, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual.

The computing server 130 performs various analysis of the genetic data and generates results regarding the genetics and genealogy of users of computing server 130. Depending on the embodiments, the computing server 130 may also be referring to as an online server, a personal genetic service server, a genealogy server, a family tree building server, and/or a social networking system. The computing server 130 receives genetic data from the genetic data extraction service server 125 and stores the genetic data in the data store of the computing server 130. The results regarding the genetics and genealogy of users may include the ethnic compositions of users, paternal and maternal genetic analysis, potential family relatives, ancestor information, analyses of DNA data, potential or identified phenotypes of users (e.g., diseases, traits, and other characteristics), etc. The computing server 130 may present or cause the user interface 115 to present the results to the users through a GUI displayed at the client device 110. The results may include graphical elements, textual information, data, and other elements such as family trees including pedigrees.

In one embodiment, the computing server 130 also allows various users to create one or more genealogical profiles of the user. The genealogical profile may include a list of individuals (e.g., ancestors, relatives, friends, and other people of interest) who are added or selected by the user and who are suggested by the computing server 130 based on the genealogical records and/or genetic records. The user interface 115 controlled by or in communication with the computing server 130 may display the individuals in a list or as a family tree such as in the form of a pedigree. In one embodiment, subject to user's privacy setting and authorization, the computing server 130 may allow the user's genetic dataset to be linked to the user profile and to one or more of the family trees. The user may also authorize the computing server 130 to analyze the user's genetic dataset.

Example Computing Server Architecture

Figure 2:
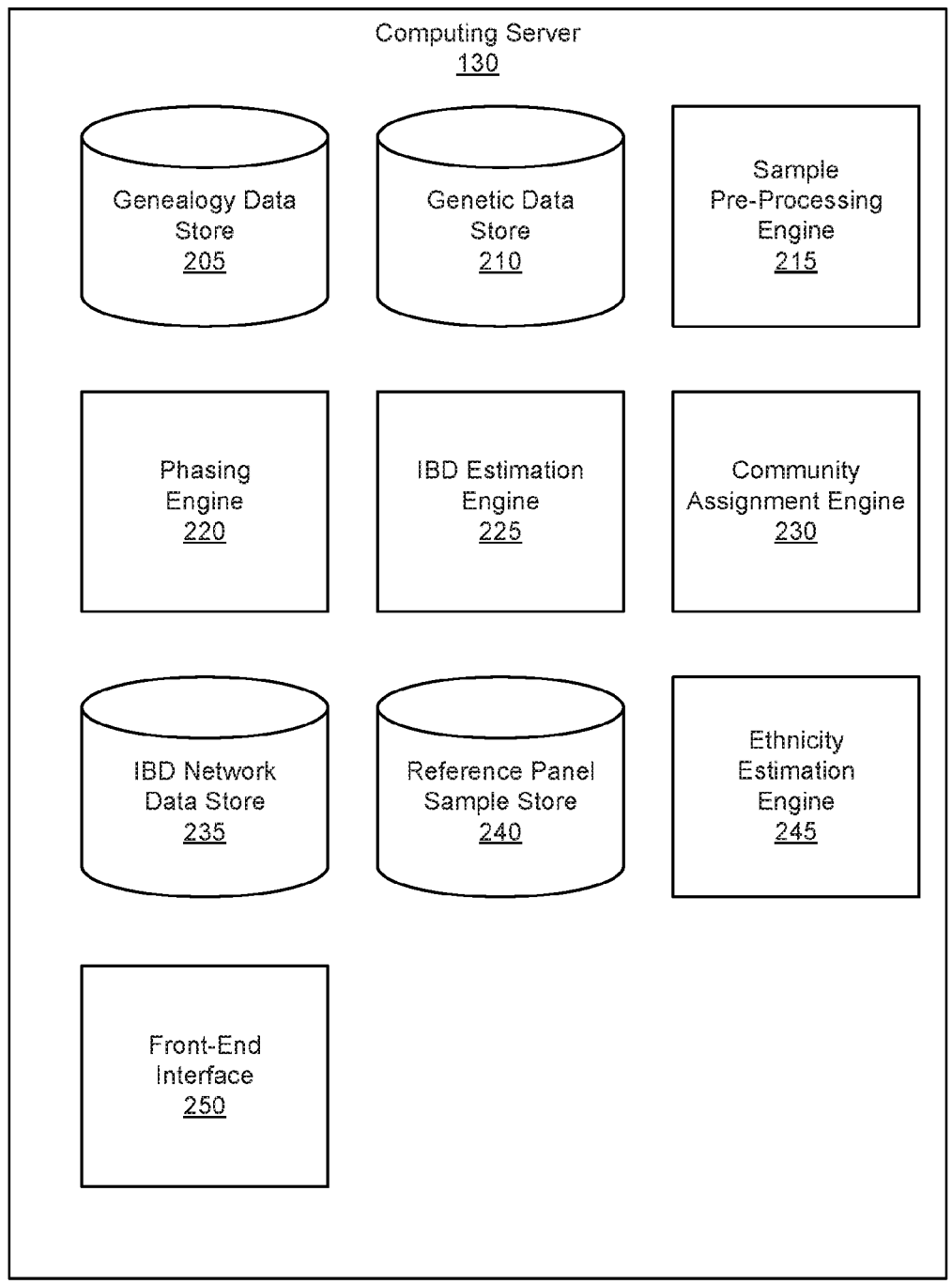
FIG. 2 is a block diagram of an architecture of an example computing system, in accordance with an embodiment.

FIG. 2 is a block diagram of an architecture of an example computing server 130, in accordance with an embodiment. In the embodiment shown in FIG. 2, the computing server 130 includes a genealogy data store 205, a genetic data store 210, a sample pre-processing engine 215, a phasing engine 220, an IBD estimation engine 225, a community assignment engine 230, an IBD network data store 235, a reference panel sample store 240, an ethnicity estimation engine 245, and a front-end interface 250. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 processes the genetic data of users to identify shared IBD segments between individuals. The computing server 130 stores various data of different individuals, including genetic data and genealogical data. The computing server 130 maintains genealogical data including user profile data in the genealogy data store 205. The amount and type of user profile data stored for each user in the genealogy data store 205 may vary based on the information provided by the corresponding user. Users may provide data via the user interface 115 of a client device 110. For example, the user may be prompted in a graphical element of a user interface to answer questions related to the user and basic information that can be processed to obtain other genealogical and survey data. Examples of genealogical data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of that individual (e.g., the recorded relationships in the family). The pedigree information associated with a user includes one or more specified nodes. Each node in the pedigree represents the individual, an ancestor of the individual who might have passed down genetic material to the individual, and the individual's other relatives such as offspring in some cases. Genealogical data may also include genetic connections among users of the computing server 130.

In addition to user-input data, genealogical data may also take other forms that are obtained from various sources such as public records and third-party data collectors. For example, genealogical records from public sources include birth records, marriage records, death records, census records, court records, probate records, adoption records, obituary records, etc. Genealogical data in the form of survey data include information about people's phenotypes, such as physical traits (e.g., height, hair, skin pigmentation, freckling, bitter taste, earlobe type, iris patterns, male pattern baldness, hair curl), wellness phenotypes (e.g., lactose tolerance, caffeine consumption, malaria resistance, norovirus resistance, muscle performance, alcohol flush), and personal preferences (e.g., likes and dislikes). Furthermore, the genealogy data store 205 may also include information inferred from the genetic samples stored in the genetic data store 210 and information received from the individuals. For example, information regarding which individuals are genetically related, how they are related, how many generations back they share common ancestors, lengths and locations of IBD segments shared, which genetic communities an individual is a part of, variants carried by the individual, and the like.

Additionally, genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

The computing server 130 maintains genetic datasets of individuals in the genetic data store 210. A genetic dataset of an individual may be a digital dataset of nucleotide data and corresponding metadata. The data may contain the whole or portions of individual's genome. The genetic data store 210 may also store a pointer to a location associated with the genealogy data store 205 associated with the individual. A genetic dataset may take different forms. In one embodiment, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of target SNP sites (e.g., allele sites) filtered from the sequencing results. A target SNP site may also be referred to as a genetic marker, which may be associated with a unique identifier. The genetic dataset may be in a form of a diploid data that include a sequencing of genotypes, such as genotypes at the target SNP sites, or the whole base pair sequence that includes genotypes at the SNP sites and other base pair sites that are not commonly associated with SNPs. The diploid dataset may be referred to as a genotype dataset. An individual's genotype may refer to a collection of diploid allele sequence of an individual. In other contexts, a genotype may be a pair of alleles present on two chromosomes for an individual at a given genetic marker such as a SNP site.

As such, each genotype at a SNP site may include a pair of alleles. The pair of alleles may be homozygous (e.g., A-A or G-G) or heterozygous (e.g., A-T, C-T). Instead of storing the actual nucleotides, the genetic data store 210 may store genetic data that are converted to bits. For many SNP sites, only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store the nucleotide that corresponds to the first allele and the nucleotide that corresponds to the second allele at a given SNP site.

A diploid dataset may also be phased into two sets of haploid data, one corresponding to a first parent side and another corresponding to a second parent side. The phased datasets may be referred to as haplotype datasets.

In one embodiment, the genetic data store 210 may additionally contain information about known variants of which individuals are carriers (e.g., the type of variant, location of the variant, phenotypes associated with the variant). This information can be obtained from the computing server 130, a third-party database or obtained using third-party software.

The sample pre-processing engine 215 receives and pre-processes data received from various sources to change the data into a format used by the computing server 130. For genealogical data, the sample pre-processing engine 215 receives data from an individual via the user interface 115 of the client device 110. To collect the user data (e.g., genealogical and survey data), the computing server 130 may cause an interactive user interface on the client device 110 to display interface elements in which users can provide genealogical data and survey data. These data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. For example, 700,000 autosomal SNPs may be identified in an individual's data and may be stored in genetic data store 210. Alternatively, in one embodiment, a genetic dataset may include at least 10,000 SNP sites. In another embodiment, a genetic dataset may include at least 100,000 SNP sites. In yet another embodiment, a genetic dataset may include at least 500,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets. An individual's haplotype may refer to a collection of alleles (e.g., a sequence of alleles) that are inherited from a parent. In one context, a haplotype may also refer to a collection of alleles that corresponds to a specific mutation in a genetic segment. In other contexts, a haplotype may further refer to a specific allele at a SNP site. For example, a sequence of haplotypes may refer to a sequence allele base pairs of an individual that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP site of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio of parents and a child because the correct phasing of the child is almost certain by comparing the child's genotypes to the parent's genetic datasets. The haplotype-cluster model may also be generated iteratively along with the phasing process with a large number of unphased genotype datasets.

By way of example, the phasing engine 220 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. patent application Ser. No. 15/591,099, entitled "Haplotype Phasing Models," filed on Oct. 19, 2015, describes one possible embodiment of haplotype phasing.

The IBD estimation engine 225 estimates the amount of shared genetic segments between a pair of individuals based on phased genotype data (e.g., haplotype datasets) that are stored in the genetic data store 210. IBD segments are chromosome segments identified in a pair of individuals that are putatively inherited from a common ancestor. The IBD estimation engine 225 retrieves a pair of haplotype datasets for each individual. The IBD estimation engine 225 may divide each haplotype dataset sequence into a plurality of windows. Each window includes a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicate the mismatch is not attributable to potential errors in phasing. The IBD estimation engine 225 determines the total length of matched segments, which may also be referred to as IBD segments. The length is measured in the genetic distance in the unit of centimorgans (cM). The computing server 130 may save data regarding individual pairs who share a length of IBD segments exceeding a predetermined threshold (e.g., 6 cM), such as in the genealogy data store 205. U.S. patent application Ser. No. 14/029,765, entitled "Identifying Ancestral Relationships Using a Continuous stream of Input," filed on Sep. 17, 2013, describes an example embodiment of IBD estimation.

Typically, individuals who are closely related share a relatively large number of IBD segments, and the IBD segments tend to have greater lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments between two individuals.

Community assignment engine 230 assigns individuals to one or more genetic communities. A genetic community may be an ethnic origin. The granularity of genetic community classification may vary depending on embodiments and methods used in assigning communities. For example, in one embodiment, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. patent application Ser. No. 15/168,011, entitled "Discovering Population Structure from Patterns of Identity-By-Descent," filed on May 28, 2016, describes one possible embodiment of community detection and assignment.

The community assignment engine 230 may also assign communities using supervised techniques. For example, genetic datasets of know genetic communities (e.g., individuals with confirmed ethnic origins) may be used as training sets that have labeled of the genetic communities. Supervised machine learning classifiers, such as logistic regressors, support vector machines, random forest classifiers, and neural networks may be trained using the training set with labels. A trained classifiers may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. Some individuals' genetic data may be the most representative of a genetic community. Their genetic datasets may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belong to a community, in determining the ethnic composition of an individual, and in determining the accuracy in any genetic data analysis, such as by computing a posterior probability of a classification result from a classifier.

A reference panel sample may be identified in different ways. In one embodiment, an unsupervised approach in community detection may apply the clustering algorithm recursively for each identified cluster until the sub-clusters contain a number of nodes that is smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to a genetic community when sampled in various runs may be classified as a reference panel sample. The community assignment engine 230 may measure the consistency in terms of a predetermined threshold. For example, if a node is classified to the same community 95% (or another suitable threshold) of times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected.

The ethnicity estimation engine 245 estimates the ancestral composition of a genetic dataset of a target individual. The genetic datasets used may be genotype datasets or haplotype datasets. For example, the ethnicity estimation engine 245 estimates the ancestral origins (e.g., ethnicity) based on the individual's SNP genotypes or haplotypes. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In one embodiment, the ethnicity estimation engine 245 divides a target genetic dataset into a plurality of windows (e.g., about 1000 windows). Each window includes a small number of SNP sites (e.g., 300 SNP sites). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of levels. Each level, representing a window, include a plurality of nodes. The nodes representing different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNP sites belongs to a second ethnicity. Each level includes multiple nodes so that there are many possible paths to traverses the directed acyclic graph.

The directed acyclic graph includes emission probabilities and transition probabilities. An emission probability associated with a node represents the likelihood that the window belongs to the ethnicity labeling the node given the observation of SNP sites in the window. The ethnicity estimation engine 245 determines the emission probabilities by comparing SNP sites in the window corresponding to the target genetic dataset to corresponding SNP sites in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. patent application Ser. No. 15/209,458, entitled "Local Genetic Ethnicity Determination System," filed on Jul. 13, 2016, describes an example embodiment of ethnicity estimation.

The front-end interface 250 may display various results determined by the computing server 130. The results and data may include the IBD affinity between a user and another individual, the community assignment of the user, the ethnicity estimation of the user, phenotype prediction and evaluation, genealogical data search, family tree and pedigree, relative profile and other information. The front-end interface 250 may be a graphical user interface (GUI) that displays various information and graphical elements. The front-end interface 250 may take different forms. In one case, the front-end interface 250 may be a software application that can be displayed at an electronic device such as a computer or a smartphone. The software application may be developed by the entity controlling the computing server 130 and be downloaded and installed at the client device 110. In another case, the front-end interface 250 may take the form of a webpage interface of the computing server 130 that allows users to access their family tree and genetic analysis results through web browsers. In yet another case, the front-end interface 250 may provide an application program interface (API).

Example IBD Network

Figure 3A:
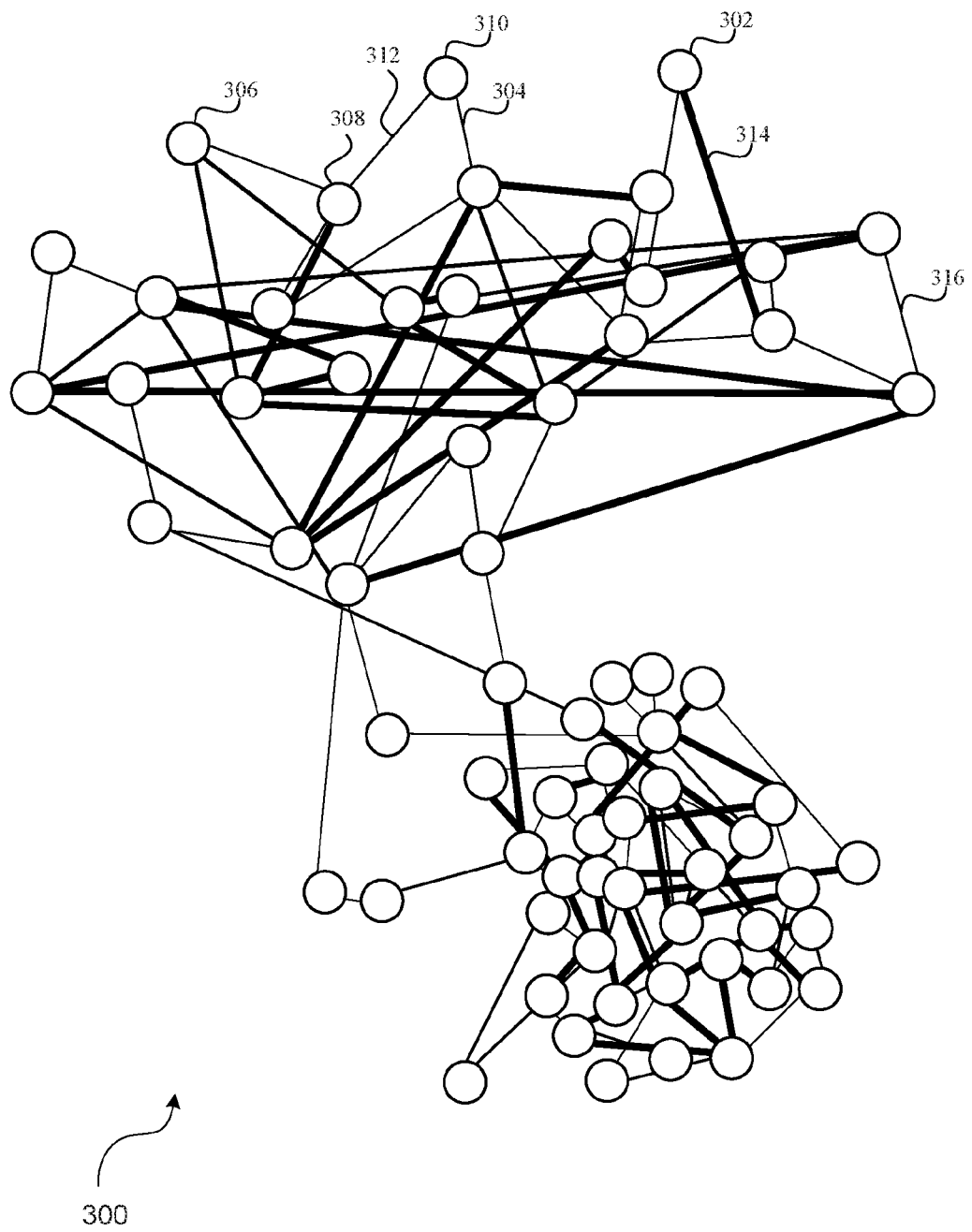
FIGS. 3A and 3B illustrate example Identity-by-Descent (IBD) networks, in accordance with an embodiment.
Figure 3B:
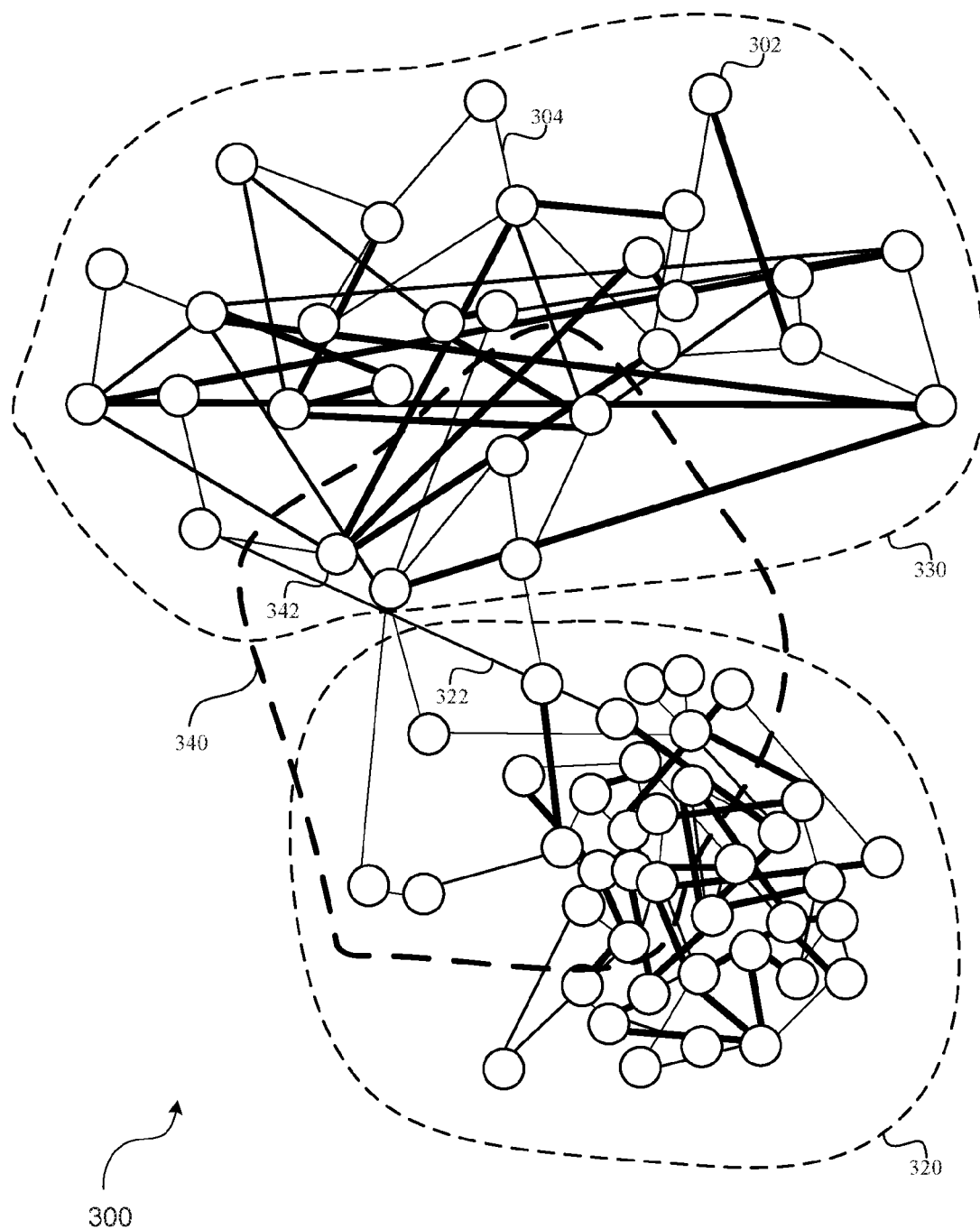

FIGS. 3A and 3B illustrate example identity-by-descent networks (IBD networks), in accordance with an embodiment. Referring to FIG. 3A, an example IBD network may be a partially connected undirected graph 300. The graph 300 includes a plurality of nodes 302. Each node represents one of the individuals having genetic data stored in the genetic data store 210. Each node 302 may correspond to the individual genetic dataset. For example, based on its data, the genetic dataset may be converted to a number of features that can be represented as a feature vector. The node 302 may correspond to the feature vector based on the vector's coordinates. Some of the nodes 302 are connected through edges 304. In an IBD network, two or more nodes 302 are connected through edges 304, but not all nodes 302 are necessarily directly connected to each other. Hence, the graph 300 may a partially connected graph. For example, a particular node 306 is connected to another node 308, but the node 306 is not connected directly to node 310. The graph 300 is for illustration only. An actual IBD network graph could include tens of thousands of nodes or even millions of nodes.

For the connected nodes, an edge 304 is associated with a weight, whose value is derived from the affinity between the genetic datasets of the two individuals represented by the two nodes. For example, the affinity between the genetic datasets of the two individuals may be the IBD affinity, which corresponds to a length of shared IBD genetic segments of the two individuals as determined by comparing the phased haplotype datasets of the two individuals. For example, a particular edge 312 represents that the two individuals represented by the nodes 308 and 310 are IBD related. The weight associated with the edge 312 corresponds to the length of shared IBD genetic segments of the two individuals. Other ways of comparing the affinity between two genetic datasets may also be possible.

The edges 304 may be associated with different weights and are illustrated as having different thicknesses in the graph 300. For example, the edge 314 is thicker than the edge 316, which indicates that the two individuals connected by the edge 314 have a higher IBD affinity than the two individuals connected by the edge 316. The computing server 130 may derive the exact values of the weights from the affinity. In one embodiment, the values of the weights may be the IBD affinity measured in centimorgan. In another embodiment, the values of the weights may be mapped or transformed from the IBD affinity. For example, the computing server 130 may normalize the weights between 0 and 1.

The mapping function between IBD affinity and edge weights may be any continuous or discontinuous function with the function domain defined by the set of possible total IBD segment lengths. In an embodiment, the computing server 130 maps the total IBD segment lengths to edge weights by: (1) choosing a target range of generations; (2) empirically assessing, using a reasonably realistic simulation, the distribution of total IBD lengths among pairs of individuals that share common ancestors within that range of generations; and (3) defining the affinity so that high weights are placed on total IBD lengths arising from familial relationships sharing common ancestors corresponding to the chosen range of generations. This has the effect of more heavily weighting the edges between relatives sharing common ancestors in the target generation range. For example, for a generation range of 0-4 generations ago, more weight is assigned to edges between relatives separated by eight meiosis events or less, and less weight is placed on nine meiosis events and more distantly related connections, where one meiosis event corresponds to a parent-child relationship, two meiosis events corresponds to siblings or to a grandparent-to-child-relationship, and so on.

In one embodiment, the IBD-to-edge-weight mapping function was chosen based on a Beta cumulative density function (CDF) (e.g., Probability (X≤x), where x is the IBD affinity between any pair of individuals) with scale parameters $\alpha=1.1$ and $\beta=10$ which defines the weights for edges in the IBD network. Other choices for the mapping from total IBD length to edge weight may result in the generation of an IBD network with different characteristics. For example, placing greater weight on more distant familial relationships might reveal structure arising from population events at different time periods.

A module of the computing system 130, such as the community assignment engine 230, generates data that represents the graph 300. The data may be in any suitable formats including a key-value pair format, a vector format, a matrix format, a tensor format, or one or more combinations thereof. For example, a node may be associated with an identifier as a key that identifies the individual represented by the node and with a value that is a feature vector generated from the genetic datasets. For N individuals, data representing the edges may be in an N×N matrix format that records the weight value at cell (i, j) for the edge connecting node i and node j. For two individuals that are not IBD related (or having IBD shared length below a threshold), the cell (i, j) could have the value 0 or nil to indicate that there is no edge connected the two nodes representing the two individual.

Inferring Genetic Communities

FIG. 3B illustrates an IBD network and an example approach in inferring communities, in accordance with an embodiment. The computing system 130 divides the nodes 302 in the graph 300 into a plurality of clusters based on the weights of the edges 304 connecting the nodes 302. For example, for illustration, the graph 300 may be divided into two clusters 320 and 330 that are enclosed by two dashed lines. Each determined cluster may represent a genetic community such as an ethnicity.

Various algorithms may be used to cluster an IBD network. Examples include any suitable unsupervised algorithms in machine learning that may be used to identify connected subsets of a network, in which the density of edges within each subset is higher than expected. Described, below, is one of the suitable methods by which clusters may be identified in an IBD network. Examples of alternative network clustering algorithms include spectral graph clustering methods. Other unsupervised or semi-supervised community detection algorithms may also be used, such as the label propagation algorithm, the connected components algorithm, the triangle counting coefficient algorithm, the balanced triads algorithm, etc.

In one embodiment, the computing server 130 identifies the communities through a recursive application of a multi-level Louvain method, which is a modularity-based community detection algorithm. In other embodiments, communities may be identified via the recursive application of another modularity-based community detection algorithm. Example modularity-based community detection algorithms include the Fast-Greedy algorithm, eigenvector based algorithm, semidefine program (SDP) based algorithm, etc.

In a modularity-based community detection algorithm, the computing server 130 identifies high modularity partitions of the graph 300. Modularity is a metric that measures how the partitions are defined based on the weights of the edges connecting the nodes in each partition. In an IBD network S that includes N nodes connected to each other via edges M each having a weight, modularity may be defined in any suitable way that measures the weights of the edges connecting two nodes that are classified to the same partition against the weights of the edges connected the nodes in one partition to the nodes in another partition. For example, in one case, the degree of modularity, Q, of a network partitioning is defined according to:

$$Q = \sum_k \sum_{(i,j) \in S_k} a_{ij} - \frac{d_i d_j}{2m} \quad (1)$$

where k is the community index, $S_k$ is the set of edges among all nodes assigned to community k, $a_{ij}$ is the weight of edge (i, j), $d_i$ is the "degree" of node i, defined to be the sum of all edge weights for edges connecting node i, and m is the sum of all "degrees".

In general, modularity may have a value that increases with the weights of the edges connecting two nodes that are classified to the same partition and that decreases with the weights of the edges connecting the nodes in one partition to the nodes in another partition. For example, in FIG. 3B, a candidate partition 320 as defined by the dashed line, which represents a candidate genetic community, may represent a well define partition. It is because most of the edges are connected to nodes that are classified into the partition 320. Only a few edges, such as edge 322 and nearby edges, connect a node that is inside the partition 320 to another node that is outside the partition 320. Also, those edges, including edge 322, are thin lines, meaning the weight values are low. Hence, based on equation (1) or other suitable definition of modularity, partition 320 has a high modularity value. In contrast, partition 340, which may represent another candidate genetic community, has a low modularity value, which indicates that the candidate genetic community is also poorly defined. It is because there are lots of edges that connect a node within the partition 340 to another node outside the partition 340. For example, the node 342 has a degree of five (5 edges) but every edge is connected to another node that is outside the partition 340. The computing server 130 uses an algorithm to adjust the partitions in the graph 300 to increase the value of modularity. The algorithm increases or heuristically maximizes the modularity associated with an IBD network. The adjusted partitions may be the final clusters of the IBD network. The algorithm may stop when the algorithm finishes a predetermined number of iterations (e.g., a number of epochs) or until the total modularity values of all partitions does not further increase (e.g., achieving convergence). The computation time associated with a community detection algorithm may grow linearly with the number of edges, M (e.g., complexity=O(M)).

The community detection algorithm divides network S comprising N nodes into C communities. The partitioning of the network into communities is denoted $(A_1, A_2, A_3, \ldots, A_C)$. Following the completion of the community detection algorithm, communities $(A_1, A_2, A_3, \ldots, A_C)$ are labeled as "valid" if they each include at least a given threshold number of nodes t. In one embodiment, a community $A_i$ with fewer than the threshold number of nodes is not considered a valid community (i.e., an "invalid" community) and is, thus, omitted from subsequent steps of the community detection analysis and model training (its constituent nodes may be left to stand alone without being labeled as a community). In one embodiment, the threshold number of nodes t is 1,000. However, in other embodiments, the threshold number is any integer number of nodes greater than 0. The set of communities labeled as valid are denoted by $(A'_1, A'_2, A'_3, \ldots, A'_{C'})$, where C' is less than or equal to C.

This threshold cutoff for a minimum size of a community may help ensure that any detected communities will contain a sufficiently large number of nodes to be interpreted as a group of historical or geographic significance. If a community has fewer than the threshold number of nodes t, any further subcommunities generated from applying an additional round of community detection algorithm would likely be the results of potentially over-fitting or over-analyzing the data. This could suggest a subpopulation might not have an analog that experts in the field would recognize. The threshold number of nodes may be anywhere between 1000 and 10,000, depending upon the exact implementation of the system and the number of samples in the IBD network 300.

In one embodiment, the community detection algorithm may be applied recursively. After applying a first round of community detection, the computing server 130 may continue to apply the community detection algorithm again to an identified cluster to generate sub-clusters. The computing server 130 may continue to repeat this process until all of the sub-clusters do not have enough members (fewer than the threshold number of nodes). The repetition of the community detection algorithm may be referred to as a hierarchical community detection approach, which will be discussed in further details in association with FIG. 7A through 9.

In one embodiment, after genetic communities and sub-communities are identified, the computing server 130 may annotate the communities based on genealogical data associated with the individuals. For example, for a community, at least some of the individuals that are represented by nodes 302 have genealogical data such as profile data, geographical data, and ancestral data stored in the genealogical data store 205 of the computing server 130. The computing server 130 may also use ethnicity estimation engine 245 to analyze the genetic datasets of community members. Based on the ethnicity and geographical origin data determined from various sources, the computing server 130 may determine that the members in a community commonly share an ethnicity and/or a geographical origin. The computing server 130 may annotate the community with the ethnicity and/or the geographical origin.

Filtering IBD Networks

Figure 4:
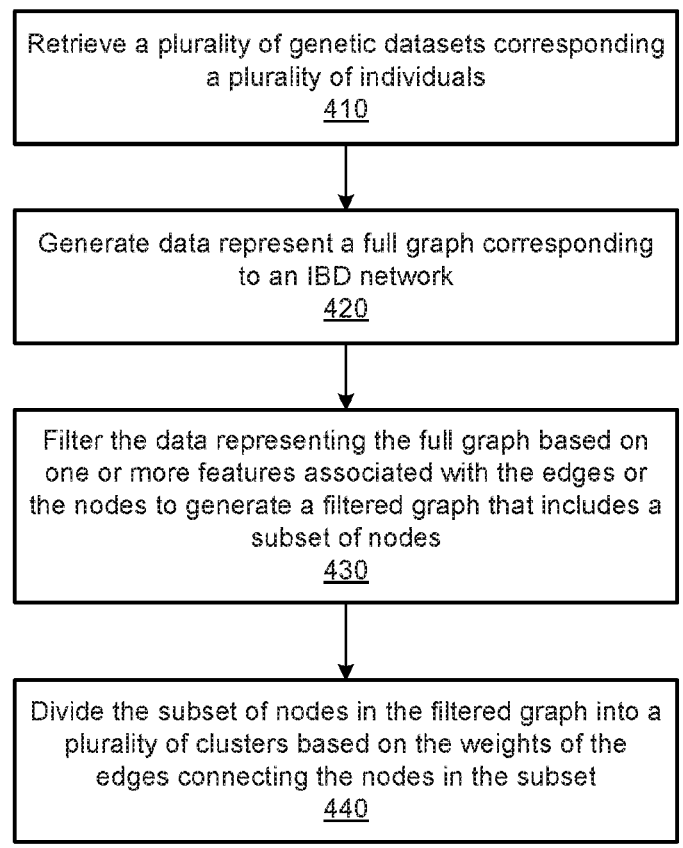
FIG. 4 illustrates a flowchart depicting an example process of filtering an IBD network, in accordance with an embodiment.
Figure 5:
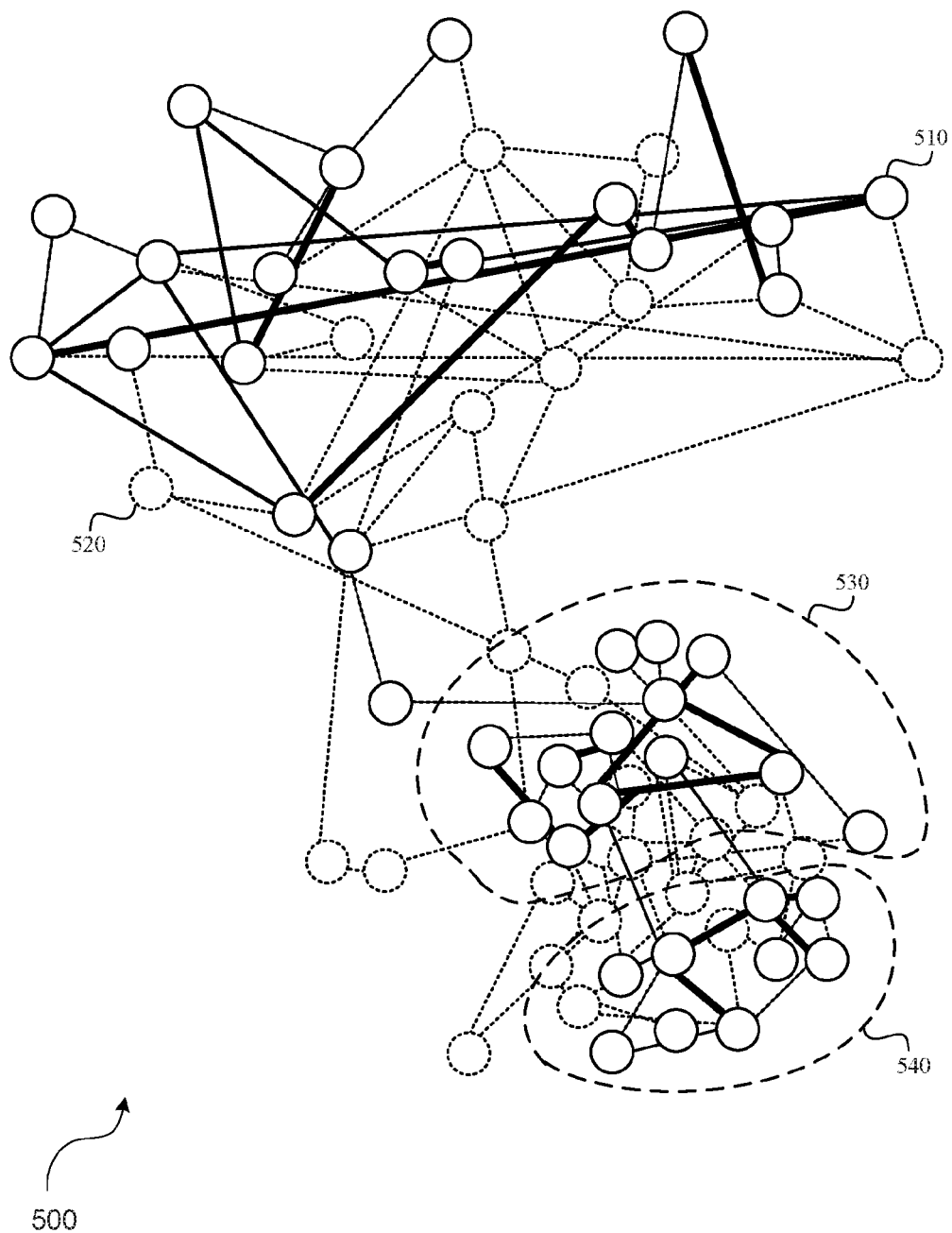
FIG. 5 illustrates an example filtered IBD network, in accordance with an embodiment.

FIG. 4 is a flowchart depicting an example process of filtering an IBD network, in accordance with an embodiment. FIG. 5 illustrates an example filtered graph, in accordance with an embodiment. Referring to FIG. 4, the computing server 130 retrieves 410 a plurality of genetic datasets corresponding to a plurality of individuals. The genetic datasets may be genotype datasets or phased haplotypes datasets of the individuals. Various numbers of genetic datasets may be retrieved. In one case, the computing server 130 may retrieve more than 1000 genetic datasets. In another case, the computing server 130 may retrieve more than 10,000 genetic datasets. In yet another case, the computing server 130 may retrieve more than hundreds of thousands or even millions of genetic datasets. The IBD affinity, which may represent the affinity between the genetic datasets of a given pair of individuals based on the length of shared IBD genetic segments of the pair of individuals, may also be determined or may have been pre-determined and stored by the computing server 130.

The computing server 130 generates 420 data that represents a full graph. The full graph may be an IBD network. The full graph may include a plurality of nodes. Each node represents one of the individuals. Two or more nodes are connected through edges. Each edge connects two nodes and is associated with a weight that is derived from the affinity between the genetic datasets of the two individuals represented by the two nodes. If the graph is an IBD network, the affinity may be IBD affinity. If the graph uses other methods to measure the similarity between the genetic datasets of two individuals, other types of measurements may be used to represent the affinity that is used to generate the weight. A full graph may represent a graph has not been filtered yet. A full graph does not require that the computing server 130 uses all genetic datasets available to generate data that represents the graph.

The computing server 130 filters 430 the data representing the full graph based on one or more features of the edges or the nodes. The filtered data represents a subset of nodes. For example, FIG. 5 illustrates a filtered graph 500 that may be filtered from a full graph 300 shown in FIG. 3A. The nodes in solid lines such as nodes 510 are selected nodes. The nodes in dashed lines such as nodes 520 are unselected nodes. The filtering may be based on one or more features associated with the edges and/or one or more features associated with the nodes.

The features used to filter a full graph may be of various types. The features may be data directly included or used in the graph or data that are related to the nodes or edges but are not used in the graph. Features directly included in the graph may be the characteristics of the affinity between two genetic datasets. For example, the edge strength (e.g., the values of the weights) may be used to filter the full graph. In contrast, features that are not used in the graph may be other characteristics of things or persons that are related to what the edges or nodes represent. For example, since the edges represent the connection or relationship between two individuals, features of an edge may be characteristics of persons or things that are commonly shared by the two individuals connected by the edge. In one embodiment, an example feature may be characteristics of ancestors who are commonly shared by the two individuals whose nodes are connected by an edge. Since the ancestors are shared by the two individuals, the ancestors' characteristics may be a feature of the edge, which represents the connection between the two individuals. An example of ancestors' characteristics is the birth year of an ancestor. If two individuals share more than one ancestors, the average birth year may be used. The average birth year is the birth year if there is only a single common ancestor. The computing server 130 may filter the data representing the full graph based on a time frame (e.g., 1800-1850) of the birth years of the common ancestors. Other ancestors' characteristics, including the geographical origin of a common ancestor, the ethnicity of the ancestor, surnames of the common ancestors, etc., may also be used to filter the graph.

Example features may also include features of the nodes. Since the nodes represent individuals, the features of the nodes may be characteristics of the individuals. Example characteristics of the individuals include the ethnicity composition of the individuals, a phenotype of the individuals (e.g., a physical trait, a disease), geographical regions at which the individuals were born, etc. In one case, the genetic dataset of an individual who is represented by a node may indicate that the length of genetic segments of the individual that are inherited from a target ethnicity exceeds a threshold (e.g., 20% of the entire genetic dataset is attributable to the target ethnicity). The computing server 130 may filter the data representing the full graph by requiring selected nodes to have at least 20% genetic data attributable to the target ethnicity.

The computing server 130 may use one or more features to filter the data representing the full graph in selecting a subset of nodes that represent a filtered graph. The computing server 130 may also combine one or more edge features and/or one or more node features to filter the full graph.

The computing server 130 divides 440 the subset of nodes in the filtered graph into a plurality of clusters based on the weights of the edges connecting the nodes in the subset. Each cluster may represent a genetic community. For example, the computing server 130 uses a community detection algorithm described above to divide the subset nodes in the filtered graph into a plurality of clusters. In one embodiment, the computing server 130 defines a plurality of partitions in the filtered graph. Each partition may represent a candidate genetic community. Initially, the partitions defined may be sub-optimal, meaning the members in the candidate community may not share enough connections or similarity. The computing server 130 determines a metric (e.g., modularity) for the partitions. The metric has a value that increases with the weights of the edges connecting two nodes that are classified to the same partition and that decreases with the weights of the edges connecting the nodes in one partition to the nodes in another partition. The computing server 130 adjusts the boundaries of partitions to increase the value of the metric. In some cases, the computing server 130 uses multiple iterations to measure the metric and adjust the partition. The final adjusted partitions may be the clusters that represent the genetic communities.

The filtering of the full graph to generate a filtered graph before a community detection algorithm is applied allows the computing server 130 to discover additional communities that may not be discoverable using the full graph. For example, referring to FIG. 5, the filtered graph 500 allows the computing server 130 to use community detection algorithm to identify and separate two communities 530 and 540 that are otherwise not separable in a full graph. Referring to FIG. 3B, the two communities 530 and 540 belongs to the cluster 320, but are not separable in the full graph 300. Using the filtering approach, the computing server 130 is able to identify populations that are not previously identifiable using a full graph. In one embodiment, the computing server 130 filters the full graph based on the birth years of the common ancestors of the individuals represented by the nodes in the graph. The computing server 130 identifies clusters in a filtered graph that represent populations in different states of the United States, such as Michigan, Wisconsin, Minnesota, Iowa, Texas, Utah, etc. By including more recent relationships, recent population structures can be identified because older relationships may cover the more recent structure when all edges are used in a graph. Using a similar approach, communities representing populations in Australia and South Africa are also identified by various filtered graphs.

Figure 6:
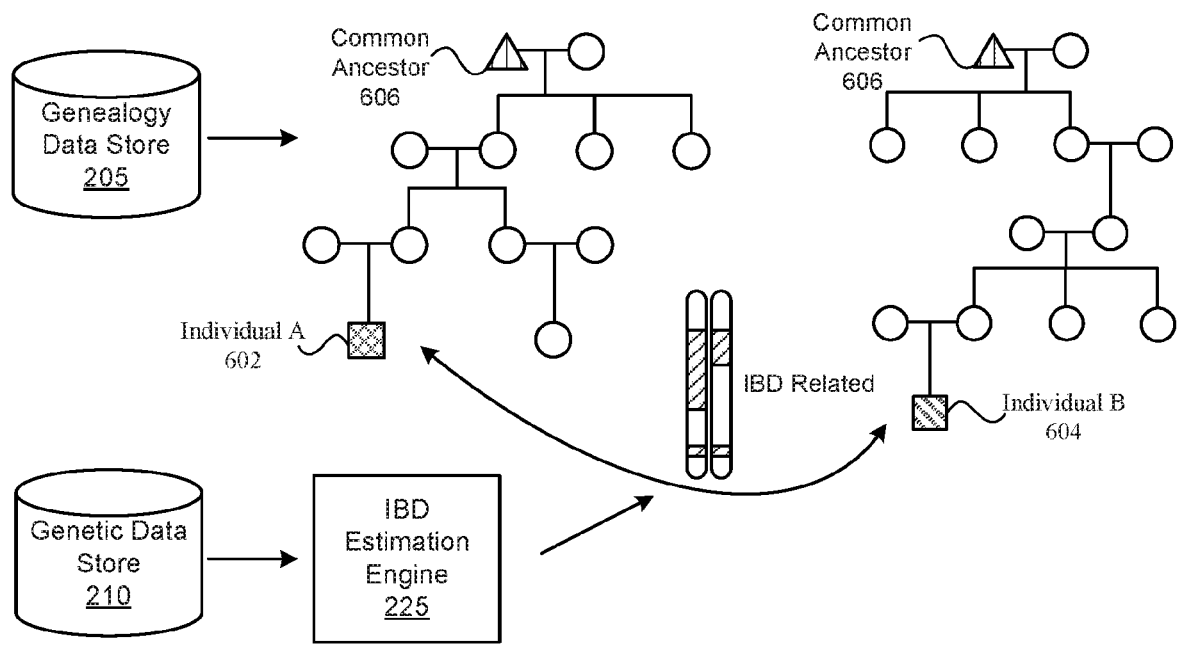
FIG. 6 is a block diagram illustrating an example process of classifying a birth year of a common ancestor of two individuals to a time frame, in accordance with an embodiment.
Figure 6:
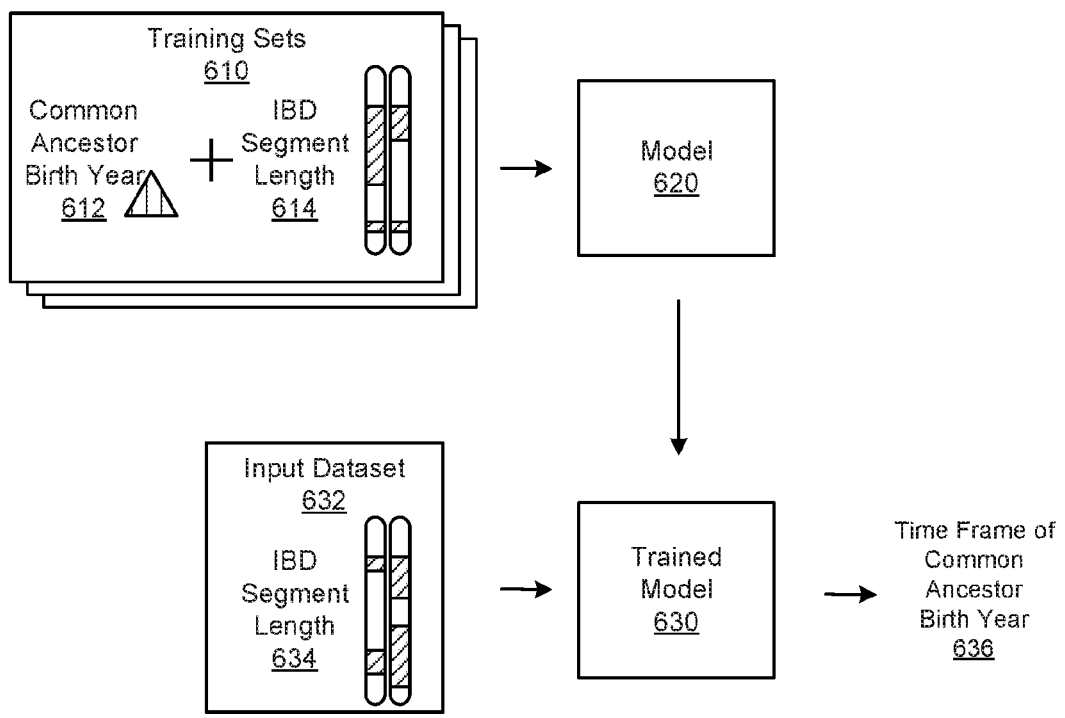

FIG. 6 is a block diagram illustrating an example process of classifying a birth year of a common ancestor of two individuals to a time frame, in accordance with an embodiment. In a graph such as an IBD network 300, the computing server 130 may not possess data regarding the birth year of all common ancestors corresponding to the edges in the graph. For example, even though the computing server 130 determines that two individuals are related IBD, the common ancestor may be unknown to the computing server 130 so that the birth year is unknown. However, since the length of IBD segments may be correlated to how many generations ago the two individuals are related, a model (e.g., a classifier) may be trained to predict the birth year of the common ancestor or to assign the common ancestor to a time frame (e.g., 1700-1800, 1800-1900). For the edges that correspond to unknown ancestors or ancestors with unknown birth years, the birth year may be estimated from the length of shared IBD genetic segments of two individuals using a model that takes the length of shared IBD genetic segments as input. After the birth year is estimated or classified to a time frame, the computing server 130 may filter a full graph and run the community detection algorithm.

The computing server 130 may use data from its genealogy data store 205 to generate labeled training sets. For example, the computing server 130 may retrieve the genetic datasets of individual A 602 and individual B 604 from the genetic data store 210. The IBD estimation engine 225 of the computing server 130 may determine, based on the genetic datasets, that individuals A and B are related IBD by a length of IBD sharing. The computing server 130 retrieves genealogy data of individuals A and B such as their family tree data. Individuals A and B may have separate family trees and may not know that they are related IBD. From the family tree data and potentially with validation of other genealogy data, the computing server 130 determines that the pair of individuals share a common ancestor 606. The common ancestor 606 has birth year data that is available in the computing server 130. For example, one of the individuals A or B may input the birth year, or the computing server 130 is able to locate the birth year of the common ancestor 606 from a public record source such as birth record certificate data. The computing server 130 generates a training set 610 that includes the common ancestor birth year 612 and the length of IBD sharing 614 as two features in the training set 610. The common ancestor birth year 612 may be used as the label of the training set 610. The computing server 130 may repeatedly identify in its data stores more pairs of individuals who are IBD related and who have a common ancestor whose birth year is known. A plurality of training sets may be generated.

The computing server 130 trains a model 620 using the training sets 610. The model 620 may be a classifier that classifies the estimated birth year into one of the possible time frames or a regressor that predicts the birth year of the common ancestor. For example, for a classifier, a logistics regression classifier, a random forest classifier, a support vector machine (SVM), a neural network, etc. may be used. The objective function of the classifier may be the errors in classifying the training sets into the correct time frame. In training of the classifier, the computing server 130 adjust the weights of the model to reduce or minimize the errors through techniques such as coordinate descent or stochastic coordinate descent (SGD). In one embodiment, a logistics regression classifier that uses IBD segment lengths 614 to predict the time frame of the birth year of the ancestors may be used. Non-linear models such as random forest and SVM may also be used. In some embodiments, the computing server 130 may use additional features to predict the birth year. For example, various genealogy data may also be helpful in predicting the frame of the birth year of a common ancestor. The computing server 130 may train a neural network that receives IBD segment length 614 and other features to predict the time frame.

After the model 620 is sufficiently trained, the trained model 630 may be used to predict the time frame of the common ancestor's birth year 636. Since the weight of an edge in an IBD network is derived from the IBD segment length, the IBD segment length is known for a given edge. For a given edge, an input dataset 632 includes the IBD segment length 634 may be input to the trained model to generate the time frame 636. After the predicted time frames are generated for the edges in a full graph of an IBD network, the computing server 130 filters the full graph based on the estimated time frame to select edges representing common ancestors who were estimated to be born within the target time frame. The computing server 130 then applies the community detection algorithm to discover genetic communities with respect to the target time frame.

For instance, the population of Connecticut that existed in the 1700s moved west into New York during the 1800s, and mixed with other populations. Existing methods did not identify a corresponding structure associated with this population migration when all matches were used. In contrast, by generating a filtered graph that corresponds to common ancestors born in the 1700s, the computing server 130 can identify a population structure in Connecticut from that time period that is associated with the migration to New York. Another example is Australia. The computing server 130 may not be able to find any communities in Australia using a full graph. However, by using only those edges from the 1800s, the computing server 130 identifies a population structure in Australia that is due to 19th-century mating patterns.

Instead of using a machine learning model, finding the time of a common ancestor between two individuals could be approximated with a population genetics model. For example, the statistical distribution of IBD shared length may be generated and the generation of the common ancestor can be predicted. The generation can be mapped to years when a population genetics model is available.

Alternative to, or in addition to, filtering a full graph by an edge feature such as common ancestor's birth year time frame, the computing server 130 may filter the full graph using a node feature such as the ethnicity composition of the individuals represented by the nodes. This approach allows the removal of noise from other groups which may be overly represented in the data store of the computing server 130. In some cases, the computing server 130 may be more popular among customers of a particular region but not as popular in another region. As such, there can be biased in the IBD network constructed and some population structures may be stronger than others. In some cases, this can make the discovery of structure in certain under-represented populations difficult. The computing server 130 may filter the individuals only those individuals of a particular ethnicity of interest. For example, better and more refined population structures in Asia can be found when a full graph is filtered to include those individuals of Asian descent. This approach results in a more refined community discovery for admixed populations.

In one embodiment, the computing server 130 may filter the nodes in a full graph by requiring the selected subset of nodes to include at least a certain percentage (e.g. 20%) of genetic data attributable to a target ethnic origin. The computing server 130 may determine the length of genetic segments of an individual that are inherited from the target ethnic origin by comparing the genetic dataset of the individual to one or more reference panel samples of the target ethnicity. For example, the computing server 130 may use ethnicity estimation engine 245 to determine the ethnic composition of the individual. For an admixed individual, the node representing the individual may be selected in multiple filtered graphs. For example, filtering the data representing the full graph to generate a first filtered graph may be based on a first target ethnicity presented in the ethnic compositions of the individuals. In addition, filtering the data representing the full graph to generate a second filtered graph may be based on a second target ethnicity presented in the ethnic compositions of the individuals. For example, the filtering criteria may require each filtered graph to include individuals that have at least 20% of target ethnicity. As a result, a node that represents an admixed individual may be present in both the first and the second filtered graphs.

Multi-Path Hierarchical Community Detection

Figure 7A:
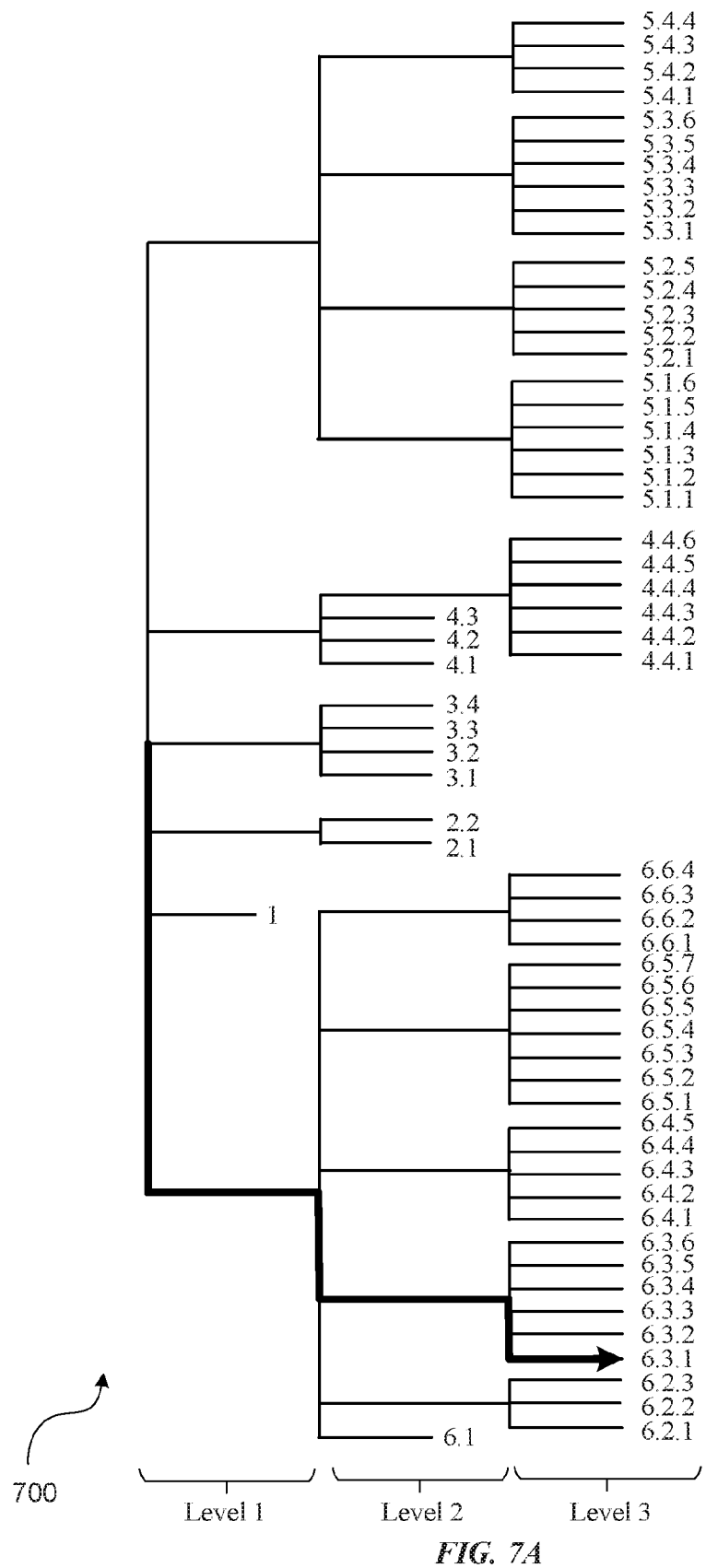
FIG. 7A illustrates a tree diagram for a single-path community detection process.

FIG. 7A through FIG. 9 illustrate an example multiple-path hierarchical community detection process, in accordance with an embodiment. FIG. 7A illustrates a tree diagram 700 for a single-path hierarchical community detection process. The tree diagram 700 includes a plurality of branches and end leaves, which are each denoted by a numerical identifier, such as "1," "2.1," "5.2.5," "6.3.4," etc. A branch represents a path to reach a leaf. The leaf represents a community or subcommunity that corresponds to a cluster in a graph such as an IBD network in a community detection process.

In a hierarchical community detection process, the computing server 130 applies the community detection algorithm (e.g., Louvain method) to a graph (full graph or filtered graph) to divide the graph into clusters that represent a set of communities. After the set of communities is determined, the computing server 130 applies the community detection algorithm again on each cluster to identify sub-clusters within a cluster. Each sub-cluster may represent a further defined genetic community. To distinguish the initial set of communities from the sub-communities, the initial set of communities may be called "level 1" communities, and the sub-communities may be called "level 2" communities. The multiple levels of communities may be viewed as hierarchical sets of clusters.

To identify a sub-community for each level 1 community $A_i'$ (i=1, 2, ..., C'), the computing server 130 generates data representing a subgraph $g_i$ for each community $A_i'$ in the set of communities $A_i'$ (i=1, 2, 3, ..., C'). The subgraph $g_i$ is defined by the subset of nodes n that are assigned to a community $A_i'$ and the subset of edges m such that (i, j) is included in the subset if both i and j are assigned to community $A_i'$.

The computing server 130 applies a clustering algorithm (e.g., modularity-based clustering) on the subgraph $g_i$ associated with the community $A_i'$. For example, if a level 1 community $A_1'$ is associated with a subgraph $g_1$, the clustering algorithm is applied to the subgraph $g_1$. After applying the clustering algorithm to each subgraph $g_i$, with i=1, 2, . . . , C', the result is a set of sub-communities (B$_1$, B$_2$, . . . B$_D$), where D is the total number of sub-communities identified in all of the subgraphs. In one embodiment, only "valid" communities exceeding a previously specified size are retained (and this may be a different (second) threshold than the (first) threshold t used for determining the level 1 communities), resulting in a final set of level 2 communities, sub-communities (B'$_1$, B'$_2$, . . . B'$_{D'}$), in which D' is less than or equal to D.

The process described above may be repeated for subsequent levels of communities as long as at least one community has greater than the threshold number of nodes t as introduced above. For example, communities at level 3 may be delineated once again to generate a subgraph g$_i$ for each level 2 community B$_i$ and applying the community detection algorithm to each subgraph g$_i$.

Following this description, an example pseudocode for the computing server 130 for a hierarchical community detection algorithm is as follows:

```
procedure community(S)
C ← Louvain(S) // Identify set of communities associated network S
for each A_i in C do
    if(Size(A_i) ≥ N && Stability(A_i) ≥ M) then
    //N is a threshold, such as N=1,000, and M is a stability threshold
        g_i ← buildSubgraph(S, A_i)
        C ← concatenate(C, community(g_i))
return C //C is an array of communities and sub-communities associated
with network S, which can be interpreted in a hierarchy of clusters.
```

In one embodiment, the procedure delineated through the example pseudocode above results in a hierarchy of communities by recursively fragmenting or subdividing groups of connected nodes. The algorithm illustrated by the pseudocode above automatically stops subdividing further when the size of the subnetwork defined by a community contains fewer than a threshold number of nodes N, which can be a user-specified variable such as 1,000 nodes. Moreover, to create a subgraph, the stability of a subnetwork should exceed a threshold M.

In a single-path hierarchal community detection approach, a node at each level of community detection is assigned to a single cluster and only the single cluster. Hence, in a single-path approach, a node representing an individual can only traverse the tree diagram 700 by a single path to a leaf. For example, FIG. 7A illustrates an example path that reaches a leaf. At level 1 (e.g., the first round of community detection algorithm), the node is assigned to the 6th cluster. In the single-path approach, the node cannot be simultaneously assigned to the 6th cluster and another cluster. Hence, the path takes the branch that represents the 6th cluster but not other clusters. At level 2 (e.g., the second round of community detection algorithm), the node is assigned to the 3rd sub-cluster of the 6th cluster (6.3). At level 3 (e.g., the third round of community detection algorithm), the node is assigned to the 1st sub-cluster of sub-cluster 6.3, reaching the leaf 6.3.1.

Figure 7B:
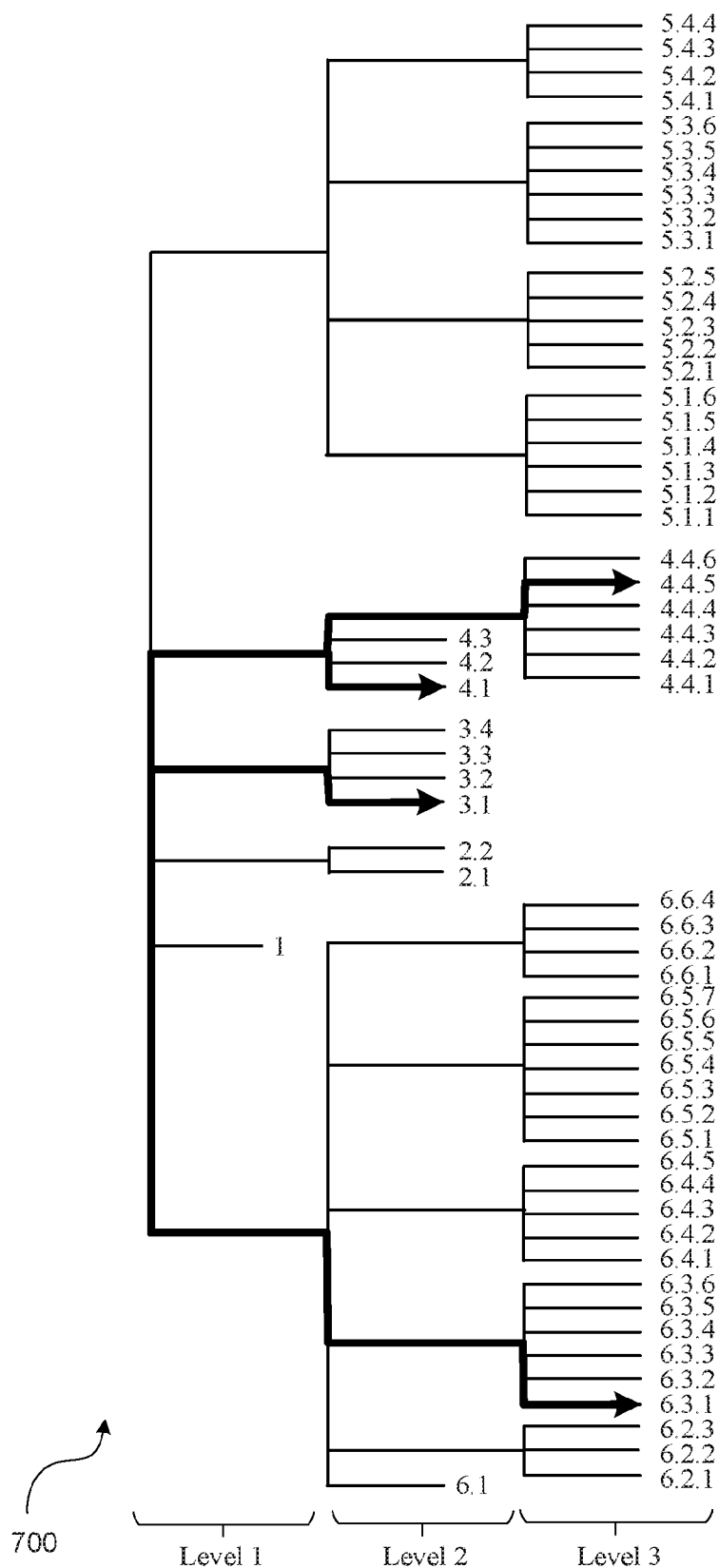
FIG. 7B illustrates a tree diagram for a multi-path community detection process, in accordance with an embodiment.

FIG. 7B illustrates a tree diagram 700 for a multi-path community detection process, in accordance with an embodiment. In this multi-path approach, a node in a graph at each level of community detection is allowed to be assigned to multi-clusters. Hence, in addition to the path that reaches the leaf 6.3.1, at level 1, the node is also assigned to the 3rd and the 4th clusters. At level 2, the node is also simultaneously assigned to the 1st and the 4th sub-cluster of the 4th cluster. After multiple rounds of community detection algorithm, the computing server 130 assigns the node to community 6.3.1, 3.1, 4.1, and 4.4.5. In other words, the node can take multiple paths to reach different communities and sub-communities. In one embodiment, at each level, the computing server 130 may first use a clustering algorithm to divide the nodes in the graph into multiple clusters and assign the target node to a single cluster. The target node is only assigned to a single cluster because methods such as the Louvain method may assign a node to only one cluster. The computing server 130 may then add the target node to additional clusters based on one or more criteria. For example, the criteria may be based on the filtering criteria as discussed above. In another embodiment, a criterion is based on a stability metric that is going to be discussed in further detail below.

Figure 8:
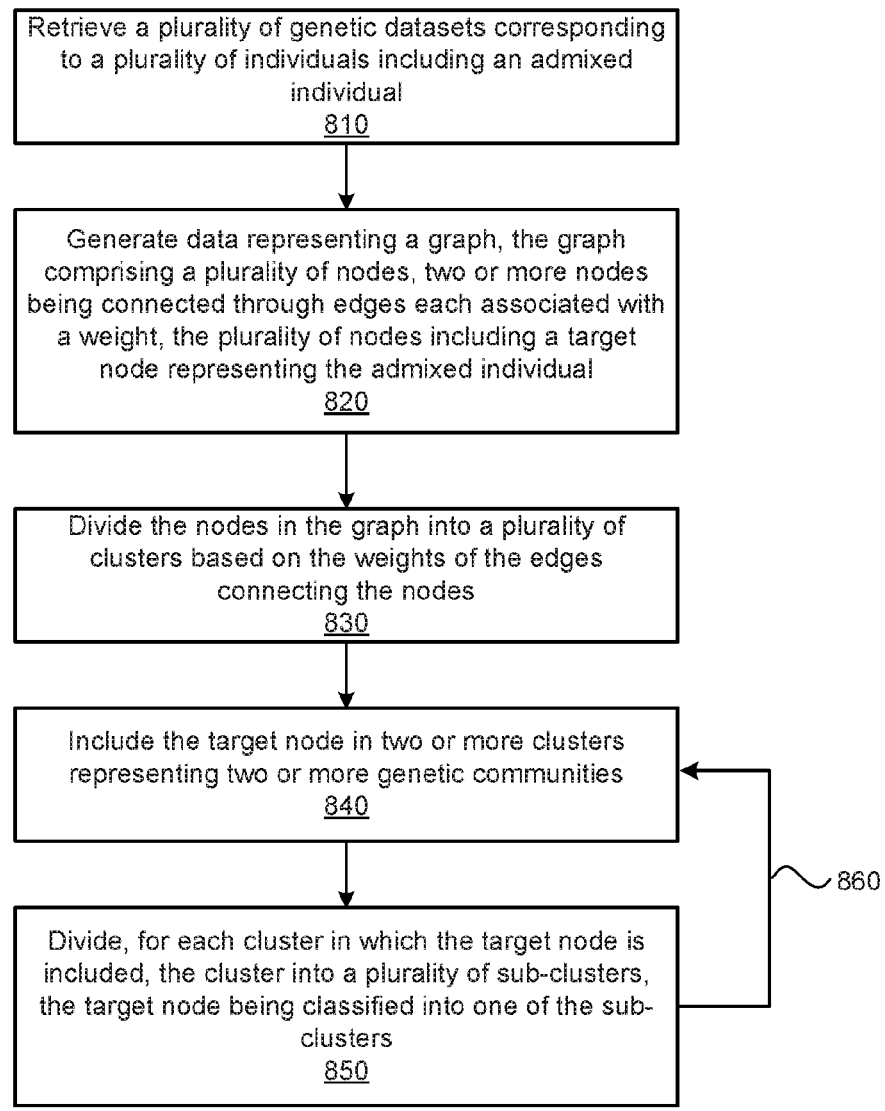
FIG. 8 is a flowchart depicting an example process of performing a multi-path community detection, in accordance with an embodiment.

FIG. 8 is a flowchart depicting an example process for performing multi-path community detection, in accordance with an embodiment. The process can be used to classify an admixed individual to more than one genetic communities. The computing server 130 retrieves 810 a plurality of genetic datasets corresponding to a plurality of individuals. At least one of the individuals is an admixed individual. The computing server 130 generates 820 data representing a graph, which may be a partially connected undirected graph. Similar to other graphs discussed in this disclosure, this graph may include a plurality of nodes. Each node represents one of the individuals. Two or more nodes are connected through edges. Each edge connects two nodes and is associated with a weight that is derived from affinity between the genetic datasets of the two individuals represented by the two nodes. The plurality of nodes includes a target node that represents the admixed individual.

The computing server 130 may apply a community detection algorithm to divide 830 the nodes in the graph into a plurality of clusters based on the weights of the edges connecting the nodes. The plurality of clusters represents a plurality of genetic communities. The computing server 130 includes 840 the target node in one or more clusters representing one or more different genetic communities. In one case, the target node is included in two or more genetic communities. For example, the computing server 130 may initially use a community detection algorithm to assign the target node of one cluster. The computing server 130 then adds the target node to additional clusters based on one or more criteria such as a stability metric.

For at least one of the clusters in which the target node is included, the computing server 130 divides 850 the cluster into a plurality of sub-clusters. For example, the computing server 130 may apply the same community detection algorithm in step 830 and 850 in dividing the graph, the clusters, or any sub-clusters into further defined sub-clusters. The computing server 130 may classify the target node into one of the sub-clusters. The target node is clustered into one or more different sub-clusters, which represent that the admixed individual is classified into one or more different genetic sub-communities of one or more ethnic origins. As indicated by the arrow 860, the computing server 130 may repeat steps 840 and 850 to further assign the target node into more sub-clusters under different paths using the hierarchical approach.

At a particular level of the hierarchical community detection process, whether a target node should be added to additional clusters may depend on a stability analysis for the target node to evaluate how stable the association between the target node and a cluster is. For example, correspond to the step 820 in FIG. 8, the computing server 130 determines whether the target node has a stability with respect to a particular cluster that exceeds a threshold. The computing server 130 will include the target node in the particular cluster in response to the stability exceeding the threshold.

The stability may take the form of a stability metric that measures the connection between a target node and a target cluster. The computing server 130 may perform step 830 to a given graph to generate a set of clusters that includes the target cluster. For the same graph, the computing server 130 randomly samples a subset of nodes from a plurality of nodes of the graph. The subset of nodes represents a sampled graph, which often includes about a certain percentage (e.g. 60-80%) of the nodes of the given graph. The computing server 130 repeats the sampling process to generate a plurality of subsets of nodes. Various subsets, which represent different sampled graphs, are generated. The computing server 130 divides each of the sampled graphs into a plurality of clusters. The dividing result may include the target cluster. It should be noted that the target cluster may not be completely identical for each sampled graph and may not be identical to the target cluster that was generated using the un-sampled graph because the application of community detection algorithm to a randomly sampled graph can produce different numbers and partitions of communities. The computing server 130 may treat a cluster that has a threshold degree of overlap in terms of the nodes assigned with the target cluster generated in the un-sampled graph as the same target cluster. As each time a certain percentage (e.g. 60-80%) of the nodes may be sampled, the target node may be sampled and selected in some of the sampled graphs. For those sampled graphs in which the target node is sampled, the computing server 130 determines the number of times the target node is classified into the target cluster. For example, the sampling and community detection process may be repeated 20 to 100 times. If the target node appears in, for example, 14 different sampled graphs, the number of times the target node is classified into the target cluster could be from 0 to 14. The computing server 130 derives the value of a stability metric of the target node with respect to the target cluster. The stability metric can be the ratio of the number of times the target node is classified into the target cluster to the number of times the target node appears in the sampled graphs. If the stability metric exceeds a threshold (e.g., 25%), the computing server 130 adds the target node to the target cluster in step 840 for another round of community detection in the multi-path hierarchical approach. A relative low threshold (e.g., lower than 50%) may be set so that the target node may be added to more than one cluster.

The computing server 130 may also use the stability analysis to determine reference panel samples for a community. For example, the same stability analysis may be performed for a target community to locate nodes that are more consistently assigned to the target community. A higher threshold (e.g., 80%, 90%) may be used for the stability metric in selecting reference panel samples. That a node is consistently assigned to the target community whenever sampled indicates that the node may serve as a representative genetic dataset for the target community. Such a node may be selected as the reference panel sample.

Figure 9:
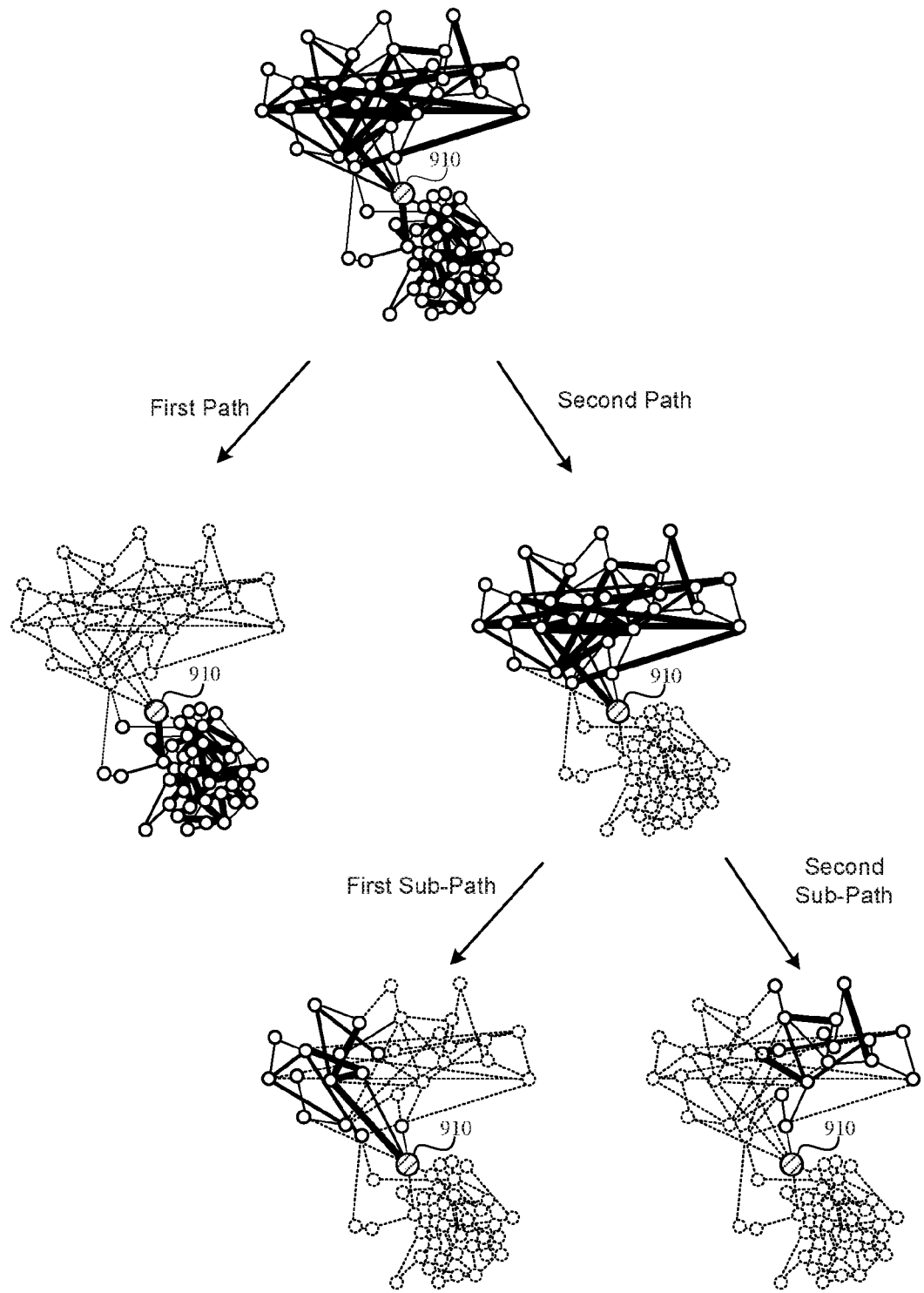
FIG. 9 illustrates a multi-path hierarchical community detection approach, in accordance with an embodiment.

FIG. 9 illustrates an example clustering process in a multi-path community detection approach, in accordance with an embodiment. The node 910 is a target node. For the first level of community detection, the target node 910 is included in two clusters. For the second path, the target node is also included into two sub-clusters. As such, FIG. 9 illustrates at least three paths to assign the target node 910 into three different communities or sub-communities.

Community Classification

Figure 10:
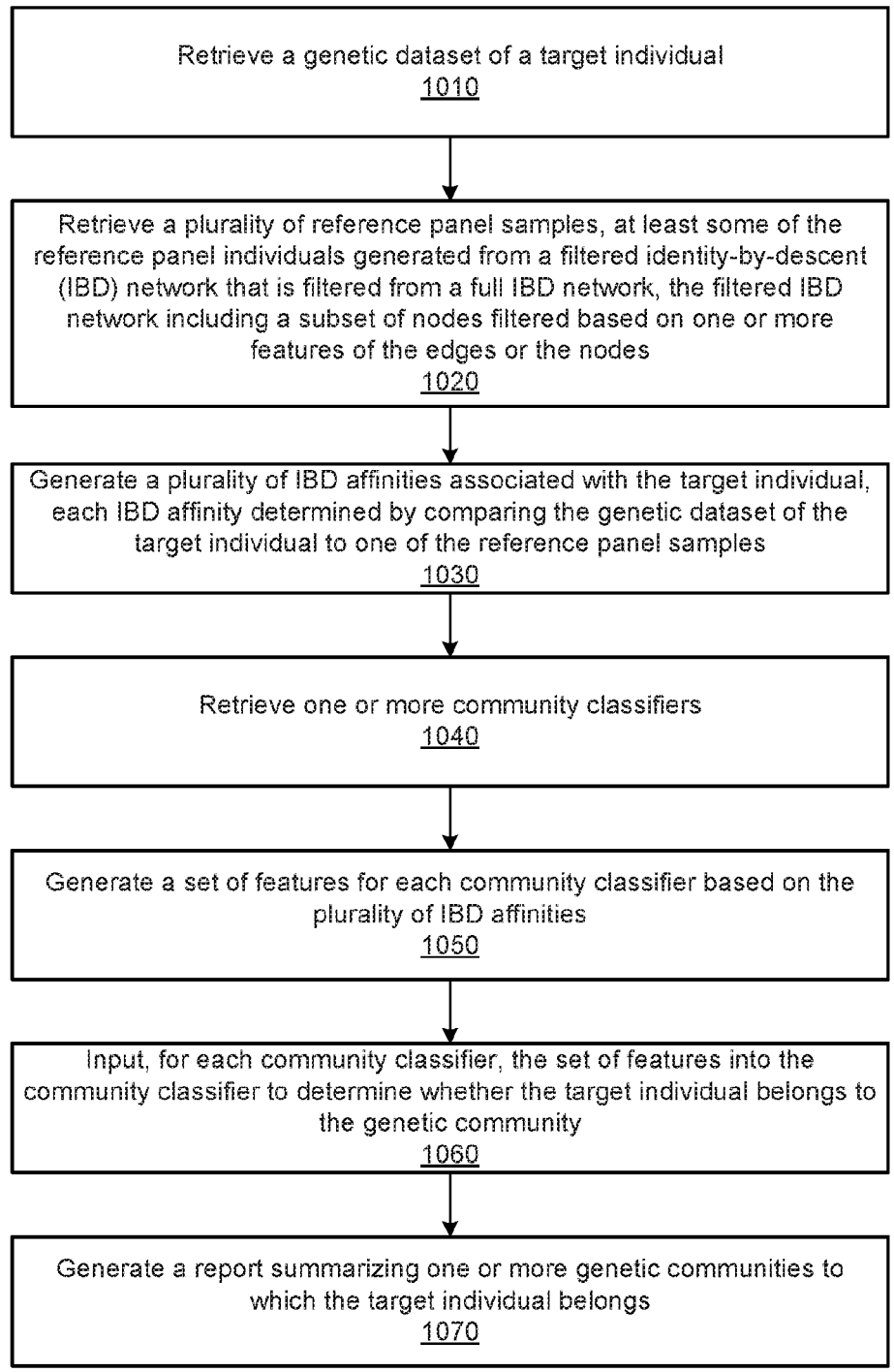
FIG. 10 is a flowchart depicting an example process of detecting an ancestral composition of an individual, in accordance with an embodiment.

FIG. 10 illustrates a flowchart depicting a process for detecting the community of a target individual, in accordance with an embodiment. The computing server 130 uses one or more trained machine learning models to compute, for a given target individual, a score (e.g., a probability) for assignment of the target individual to a community. The model may be used classify existing individuals, for example, someone present in the genetic data store 210, or new users who have submitted their DNA samples for inclusion in the computing server 130.

The computing server 130 retrieves 1010 a genetic dataset of a target individual. The computing server 130 also retrieves 1020 a plurality of reference panel samples from reference panel sample store 240. Each reference panel sample represents a reference panel individual. At least some of the reference individuals are generated from a filtered IBD network that is filtered from a full IBD network. The filtered IBD network includes a subset of nodes filtered based on one or more features of the edges or the nodes, as discussed in FIG. 4 through FIG. 9.

The computing server 130 generates 1030 IBD affinities associated with the target individual. Each IBD affinity is determined by comparing the genetic dataset of the target individual to one of the reference panel samples, such as by comparing the phased genetic datasets of the target individual and the reference panel sample. The computing server 130 retrieves 1040 one or more community classifiers. Each community classifier can be a model trained to determine whether an individual belongs to a genetic community. The computing server 130 generates 1050 a set of features for each community classifier. In some embodiments, some classifiers may receive the IBD affinities or the genetic datasets of the target individual as the features. In other embodiments, the computing server 130 may convert the IBD affinities (and, in some instances, the ethnicity estimates) and genetic datasets into a feature vector according to the features selected for each of the models. Each model receives a different feature vector depending on which features were selected and used to train that particular model.

For a community or sub-community identified, the computing server 130 may use training sets with selected features to train a classifier model for that community. By way of example, the computing server 130 may select features that are estimated to have high prediction ability as the features used in classification. The features may be extracted from the genetic datasets, the IBD affinity values, the ethnicity estimation, etc. A set of features may be different for various communities. Examples of algorithms that may be used to implement the feature selection include, but are not limited to, sparse penalized regression (e.g., Lasso), a forward/stepwise regression method, recursive feature elimination, and regularized trees. The computing server 130 uses the set of features selected for that community to train a corresponding model. After training is completed, the model is able to generate, for a target individual, a score or a likelihood for predicting assignment of that individual to the community. In one embodiment, the model outputs a probability (a real number between 0 and 1), in which a number close to 1 indicates that the individual is classified to the community with high confidence, and a number close to 0 indicates with high confidence that the individual is not a member of the community.

The training sets include features of known individuals who have been classified to one or more communities. Individuals who are a part of the model's targeted community are assigned training labels of "1," indicating that they should be classified into the community. Individuals that are part of any other community are assigned training labels of "0," indicating that they should not be classified into the community. In one case, the classification of the training labels may be based on the stability score of the individual associated with a particular community. For example, in one embodiment, individuals who have the stability scores for a community that are larger than a first threshold is assigned with the training labels of "1" while individuals who have the stability scores that are smaller than a second threshold is assigned with the training labels of "2." In one case, individuals who have the stability scores between the first and second thresholds are not used for training. In one embodiment, individuals are drawn from an IBD network (filtered or full) and/or reference panel samples at random to construct the training set provided as input to the model training algorithm and for use in training the model. In other embodiments, the input data may be selected differently. The data related to the individuals are converted to features for the model.

A suitable machine learning model structure, supervised or unsupervised, may be used to train the models. Example structures include, but are not limited to, random forests, support vector machines (SVM), logistic regression, and neural networks. Each model may be associated with a set of weights. The training process includes determining the classification results using the training sets and adjusting the weights of the model to reduce or minimize the errors of the model based on the training labels. The adjustment of the weights may include one or more techniques such as coordinate descent, stochastic coordinate descent, etc. Training may be determined to be completed after finishing a set number of iterations (e.g., numbers of epochs) or after the error rate no longer improves (e.g., the model has converged). A classifier model can be trained and specialized in one community, although a multi-class classifier for multiple communities is also possible. For a plurality of communities, multiple models may be trained. The computing server 130 stores the models, including the trained model weights, as the community classifiers.

After the community classifiers have been trained 540, the computing server 130 inputs 1060, for each community classifier, the set of features associated with the target individual into the community classifier to determine whether the target individual belongs to the genetic community. This may include computing a score such as a probability for each model. In one implementation, an individual is classified as belonging to a given community if the probability computed by the trained model exceeds a threshold numerical value. The threshold for classifying individuals to communities may be the same or different for each model. The output of the community prediction module may include both the classification and the posterior probability for each community (e.g., the confidence level on whether the classification is correct).

The computing server 130 generates 1070 a report summarizing one or more genetic communities to which the target individual belongs. Due to a variety of factors such as the broad genetic diversity of the user base, the varying quality of the IBD affinities for different users, and the heterogeneity in composition of the communities identified in the IBD network, an individual may be predicted to be a member of zero, one, or more communities. In one embodiment, the output of the community prediction module may be reported to a user via a generated document or a GUI. Data reported in the document or GUI may also draw on annotations associated with the community, as well as historical or geographic interpretations drawing from summaries of the annotations associated with the community. This may include geographical features or regions distinguishing the community, and other historical, social or economic features characteristic of the community that may or may not be informed by the annotations. The computing server 130 may additionally produce reports that summarize IBD connections and other genetic estimates relevant to each community. For example, an estimate of the number of second cousins that are classified as belonging to the same community as the user may be reported.

Computing Machine Architecture

Figure 11:
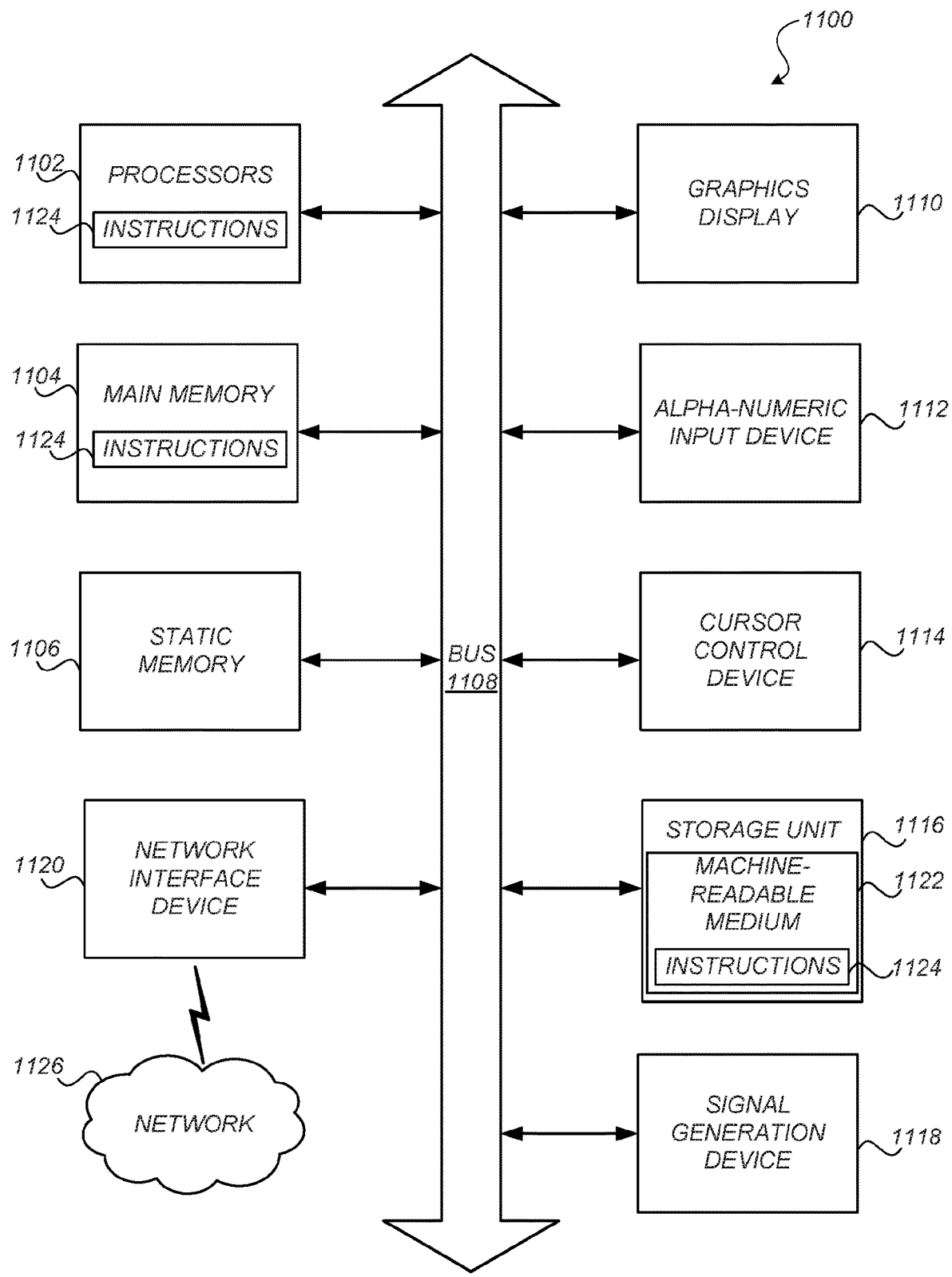
FIG. 11 is a block diagram of an example computing device, in accordance with an embodiment.

FIG. 11 is a block diagram illustrating components of an example computing machine that is capable of reading instructions from a computer-readable medium and execute them in a processor (or controller). A computer described herein may include a single computing machine shown in FIG. 11, a virtual machine, a distributed computing system that includes multiples nodes of computing machines shown in FIG. 11, or any other suitable arrangement of computing devices.

By way of example, FIG. 11 shows a diagrammatic representation of a computing machine in the example form of a computer system 1100 within which instructions 1124 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 11 may correspond to any software, hardware, or combined components shown in FIGS. 1 and 2, including but not limited to, the client device 110, the computing server 130, and various engines, interfaces, terminals, and machines shown in FIG. 2. While FIG. 11 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1124 that specify actions to be taken by that machine. Further, while only a single machine is illustrated, the term "machine" and "computer" may also be taken to include any collection of machines that individually or jointly execute instructions 1124 to perform any one or more of the methodologies discussed herein.

The example computer system 1100 includes one or more processors 1102 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1100 may also include a memory 1104 that store computer code including instructions 1124 that may cause the processors 1102 to perform certain actions when the instructions are executed, directly or indirectly by the processors 1102. Instructions can be any directions, commands, or orders that may be stored in different forms, such as equipment-readable instructions, programming instructions including source code, and other communication signals and orders. Instructions may be used in a general sense and are not limited to machine-readable codes.

One and more methods described herein improve the operation speed of the processors 1102 and reduces the space required for the memory 1104. For example, the machine learning methods described herein reduces the complexity of the computation of the processors 1102 by applying one or more novel techniques that simplify the steps in training, reaching convergence, and generating results of the processors 1102. The algorithms described herein also reduces the size of the models and datasets to reduce the storage space requirement for memory 1104.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1100 may include a main memory 1104, and a static memory 1106, which are configured to communicate with each other via a bus 1108. The computer system 1100 may further include a graphics display unit 1110 (e.g., a plasma display panel (PDP), a liquid crystal display (LCD), a projector, or a cathode ray tube (CRT)). The graphics display unit 1110, controlled by the processors 1102, displays a graphical user interface (GUI) to display one or more results and data generated by the processes described herein. The computer system 1100 may also include alphanumeric input device 1112 (e.g., a keyboard), a cursor control device 1114 (e.g., a mouse, a trackball, a joystick, a motion sensor, or other pointing instrument), a storage unit 1116 (a hard drive, a solid state drive, a hybrid drive, a memory disk, etc.), a signal generation device 1118 (e.g., a speaker), and a network interface device 1120, which also are configured to communicate via the bus 1108.

The storage unit 1116 includes a computer-readable medium 1122 on which is stored instructions 1124 embodying any one or more of the methodologies or functions described herein. The instructions 1124 may also reside, completely or at least partially, within the main memory 1104 or within the processor 1102 (e.g., within a processor's cache memory) during execution thereof by the computer system 1100, the main memory 1104 and the processor 1102 also constituting computer-readable media. The instructions 1124 may be transmitted or received over a network 1126 via the network interface device 1120.

While computer-readable medium 1122 is shown in an example embodiment to be a single medium, the term "computer-readable medium" should be taken to include a single medium or multiple media (e.g., a centralized or distributed database, or associated caches and servers) able to store instructions (e.g., instructions 1124). The computer-readable medium may include any medium that is capable of storing instructions (e.g., instructions 1124) for execution by the processors (e.g., processors 1102) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the disclosed embodiments but also any other combination of features from different embodiments. Various features mentioned in the different embodiments can be combined with explicit mentioning of such combination or arrangement in an example embodiment. Furthermore, any of the embodiments and features described or depicted herein can be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. patent application Ser. No. 15/591,099, entitled "Haplotype Phasing Models," filed on Oct. 19, 2015, (2) U.S. patent application Ser. No. 15/168,011, entitled "Discovering Population Structure from Patterns of Identity-By-Descent," filed on May 28, 2016, (3) U.S. patent application Ser. No. 15/209,458, entitled "Local Genetic Ethnicity Determination System," filed on Jul. 13, 2016, and (4) U.S. patent application Ser. No. 14/029,765, entitled "Identifying Ancestral Relationships Using a Continuous stream of Input," filed on Sep. 17, 2013.

What is claimed is:

1. A computer-implemented method, comprising:
    retrieving a plurality of genetic datasets corresponding to a plurality of individuals;
    generating a full graph, the full graph comprising a plurality of nodes and a plurality of edges, each node representing one of the individuals and each edge connecting two nodes and being associated with a weight that is derived from affinity between the genetic datasets of the two individuals represented by the two nodes;
    filtering the full graph based on one or more features associated with any of the plurality of edges or the plurality of nodes to generate a filtered graph comprising a subset of the plurality of nodes; and
    dividing the subset of nodes in the filtered graph into a plurality of clusters using a machine learning model, the machine learning model configured to partition the subset of nodes into the plurality of clusters based on respective weights of the edges connecting nodes within the subset of nodes, each cluster in the plurality of clusters representing a genetic community.

2. The computer-implemented method of claim 1, wherein the affinity between the genetic datasets of the two individuals corresponds to a length of shared identity-by-descent (IBD) genetic segments of the two individuals as determined by comparing the genetic datasets of the two individuals.

3. The computer-implemented method of claim 1, wherein filtering the full graph is based on a feature of the edges, and wherein the feature, for each edge, corresponds to a time frame assigned to an estimated average of birth years of common ancestors of the two individuals represented by the two nodes connected by the edge.

4. The computer-implemented method of claim 3, wherein the time frame, for at least one edge, is determined from a length of shared identity-by-descent (IBD) genetic segments of the two individuals as determined by comparing the genetic datasets of the two individuals.

5. The computer-implemented method of claim 3, wherein the time frame, for at least one edge, is determined by a second machine learning model using a length of shared identity-by-descent (IBD) genetic segments of the two individuals as an input.

6. The computer-implemented method of claim 5, wherein training of the second machine learning model comprises:
    identifying, based on genetic datasets of users, a plurality of pairs of users are related IBD by a length of IBD sharing;
    retrieving family tree data of the pairs of users;
    determining that each pair of users shares one or more common ancestors;
    identifying the common ancestors who have data of birth years available;
    generating training sets comprising a time frame of the birth years of the common ancestor and the length of IBD sharing; and
    training the second machine learning model using the training sets.

7. The computer-implemented method of claim 1, wherein filtering the full graph is based on a feature of the nodes, and wherein the feature, for each node, corresponds to the genetic dataset of the individual represented by the node, the genetic dataset indicating that a length of genetic segments of the individual that are inherited from a target ethnicity exceeding a threshold.

8. The computer-implemented method of claim 7, wherein the length of genetic segments of the individual that are inherited from the target ethnicity is determined by comparing the genetic dataset to one or more reference panel samples of the target ethnicity.

9. The computer-implemented method of claim 1, wherein the filtered graph is a first filtered graph, and wherein filtering the full graph is based on a first target ethnicity presented in ethnic compositions of individuals, and wherein the computer-implemented method further comprises:
    filtering the full graph based on a second target ethnicity presented in ethnic compositions of individuals to generate a second filtered graph, wherein at least one node in the second filtered graph is also present in the first filtered graph.

10. The computer-implemented method of claim 1, wherein dividing the subset of nodes in the filtered graph into the plurality of clusters comprises:
    defining a plurality of partitions in the filtered graph, each partition representing a candidate genetic community;
    determining a metric for the partitions, the metric being a value that increases with the weights of the edges connecting two nodes that are classified to a same partition and that decreases with the weights of the edges connecting the nodes in one partition to the nodes in another partition; and
    adjusting the plurality of partitions to increase the value of the metric, the adjusted partitions being the plurality of clusters.

11. A computer-implemented method, comprising:
retrieving a plurality of genetic datasets corresponding to a plurality of individuals, the plurality of individuals including an admixed individual;
generating a graph, the graph comprising a plurality of nodes and a plurality of edges, each node representing one of the individuals and each edge connecting two nodes and being associated with a weight that is derived from affinity between the genetic datasets of the two individuals represented by the two nodes, the plurality of nodes including a target node representing the admixed individual;
dividing the nodes in the graph into a plurality of clusters using a machine learning model, the machine learning model configured to partition the nodes into the plurality of clusters based on respective weights of the edges connecting nodes, the plurality of clusters representing a plurality of genetic communities;
including the target node in one or more clusters representing one or more genetic communities of the plurality of genetic communities;
dividing, for at least one of the clusters in which the target node is included, the at least one of the clusters into a plurality of sub-clusters, the target node being classified into one or more sub-clusters, wherein the target node being classified into one or more different sub-clusters represents the admixed individual being classified into one or more different genetic sub-communities of one or more ethnic origins.

12. The computer-implemented method of claim 11, wherein including the target node in one or more clusters comprises:
determining whether the target node has a stability with respect to a target cluster exceeding a threshold; and
including the target node in the target cluster responsive to the stability exceeding the threshold.

13. The computer-implemented method of claim 12, determining whether the target node has the stability with respect to the target cluster exceeding the threshold comprises:
generating a plurality of subsets of nodes, each subset of nodes sampled from the plurality of nodes in the graph, each subset of nodes representing a sampled graph;
dividing each of the sampled graphs into a second plurality of clusters, one of the second plurality of clusters corresponding to the target cluster;
determining, for the sampled graphs in which the target node is sampled, a number of times the target node is classified into the target cluster;
deriving the stability of the target node with respect to the target cluster from the number of times; and
comparing the stability of the target node to the threshold.

14. The computer-implemented method of claim 11, wherein dividing the nodes in the graph into the plurality of clusters comprises:
defining a plurality of partitions in the graph, each partition representing a candidate genetic community;
determining a metric for the partitions, the metric being a value that increases with the weights of the edges connecting two nodes that are classified to a same partition and that decreases with the weights of the edges connecting the nodes in one partition to the nodes in another partition; and
adjusting the plurality of partitions to increase the value of the metric, the adjusted partitions being the clusters.

15. The computer-implemented method of claim 11, wherein the machine learning model used in dividing the nodes in the graph into the plurality of clusters is used to divide the at least one of the clusters into the plurality of sub-clusters.

16. The computer-implemented method of claim 11, wherein the affinity between the genetic datasets of the two individuals corresponds to a length of shared identity-by-descent (IBD) genetic segments of the two individuals as determined by comparing the genetic datasets of the two individuals.

17. The computer-implemented method of claim 11, wherein the graph is a partially connected undirected graph.

18. A computer-implemented method, comprising:
retrieving a genetic dataset of a target individual;
retrieving a plurality of reference panel samples, each reference panel sample representing a reference panel individual, at least one or more of the reference panel individuals generated from a filtered identity-by-descent (IBD) network that is filtered from a full IBD network, the full IBD network comprising a plurality of nodes and a plurality of edges, each node representing an individual and each edge connecting two nodes and being associated with a weight that is derived from IBD affinity between the two individuals represented by the two nodes, the filtered IBD network including a subset of nodes filtered based on one or more features of the edges or the nodes, the filtered IBD network being further partitioned into a plurality of clusters using a machine learning model;
generating a plurality of IBD affinities associated with the target individual, each IBD affinity determined by comparing the genetic dataset of the target individual to one of the reference panel samples;
retrieving a community classifier, the community classifier comprising a second machine learning model configured to determine whether an individual belongs to a genetic community;
generating a set of features associated with the target individual, the set of features generated based on the plurality of IBD affinities;
inputting the set of features into the community classifier to determine whether the target individual belongs to the genetic community; and
generating a report summarizing one or more genetic communities to which the target individual belongs.

19. The computer-implemented method of claim 18, wherein the filtered IBD network is filtered based on a feature of the edges, and the feature, for each edge, corresponds to a time frame assigned to an estimated average of birth years of common ancestors of the two individuals represented by the two nodes connected by the edge.

20. The computer-implemented method of claim 18, wherein the filtered IBD network is filtered based on a feature of the nodes, and the feature, for each node, corresponds to the genetic dataset of the individual represented by the node, the genetic dataset indicating that a length of genetic segments of the individual that are inherited from a target ethnicity exceeding a threshold.

* * * * *